(12) United States Patent
Hartman

(10) Patent No.: US 9,205,079 B2
(45) Date of Patent: Dec. 8, 2015

(54) HEPATITIS B ANTIVIRAL AGENTS

(71) Applicant: Novira Therapeutics, Inc., Doylestown, PA (US)

(72) Inventor: George D. Hartman, Lansdale, PA (US)

(73) Assignee: Novira Therapeutics, Inc., Doylestown, PA (US)

( * ) Notice: Subject to any disclaimer, the term of this patent is extended or adjusted under 35 U.S.C. 154(b) by 0 days.

(21) Appl. No.: 14/642,393

(22) Filed: Mar. 9, 2015

(65) Prior Publication Data

US 2015/0174115 A1    Jun. 25, 2015

Related U.S. Application Data

(62) Division of application No. 14/206,496, filed on Mar. 12, 2014, now Pat. No. 8,993,771.

(60) Provisional application No. 61/778,144, filed on Mar. 12, 2013.

(51) Int. Cl.
| | |
|---|---|
| *C07D 401/00* | (2006.01) |
| *A61K 31/454* | (2006.01) |
| *C07D 401/12* | (2006.01) |
| *A61K 31/404* | (2006.01) |
| *A61K 45/06* | (2006.01) |

(52) U.S. Cl.
CPC ............ *A61K 31/454* (2013.01); *A61K 31/404* (2013.01); *A61K 45/06* (2013.01); *C07D 401/12* (2013.01)

(58) Field of Classification Search
CPC ... C07D 401/12; C07D 209/08; C07D 209/10
USPC ..................... 546/273.4; 576/277.4
See application file for complete search history.

(56) References Cited

U.S. PATENT DOCUMENTS

| | | | |
|---|---|---|---|
| 4,569,940 A | 2/1986 | Watts | |
| 5,272,167 A | 12/1993 | Girijavallabhan et al. | |
| 5,607,929 A | 3/1997 | Nicol et al. | |
| 5,919,970 A | 7/1999 | Song et al. | |
| 5,939,423 A | 8/1999 | Karlin et al. | |
| 6,650,463 B2 | 11/2003 | Obikawa et al. | |
| 7,186,735 B2 | 3/2007 | Strobel et al. | |
| 7,338,956 B2 | 3/2008 | Strobel et al. | |
| 7,595,322 B2 | 9/2009 | Morgan et al. | |
| 7,888,373 B2 | 2/2011 | Morgan et al. | |
| 8,084,457 B2 | 12/2011 | Choidas et al. | |
| 8,097,728 B2 | 1/2012 | Gu et al. | |
| 8,101,620 B2 | 1/2012 | Morgan et al. | |
| 8,404,747 B2 | 3/2013 | Kazantsev et al. | |
| 8,609,668 B2 | 12/2013 | Cuconati et al. | |
| 8,629,274 B2 | 1/2014 | Hartman et al. | |
| 8,993,771 B2 * | 3/2015 | Hartman ............. | C07D 401/12 546/273.4 |
| 2004/0039009 A1 | 2/2004 | Jagtap et al. | |
| 2005/0009871 A1 | 1/2005 | Ramesh et al. | |
| 2005/0054850 A1 | 3/2005 | Wu et al. | |
| 2005/0239833 A1 | 10/2005 | Kazantsev et al. | |
| 2007/0142440 A1 | 6/2007 | Burgdorf et al. | |
| 2009/0163545 A1 | 6/2009 | Goldfarb | |
| 2011/0009622 A1 | 1/2011 | Jitsuoka et al. | |
| 2011/0184019 A1 | 7/2011 | Zitzmann et al. | |
| 2011/0189771 A1 | 8/2011 | Block et al. | |
| 2011/0275630 A1 | 11/2011 | Matulenko et al. | |
| 2013/0142827 A1 | 6/2013 | Block et al. | |
| 2013/0267517 A1 | 10/2013 | Guo et al. | |
| 2013/0303552 A1 | 11/2013 | Xu et al. | |
| 2014/0178337 A1 | 6/2014 | Hartman et al. | |
| 2014/0179665 A1 | 6/2014 | Hartman et al. | |
| 2014/0275167 A1 | 9/2014 | Hartman et al. | |

FOREIGN PATENT DOCUMENTS

| | | |
|---|---|---|
| CN | 102093320 A | 6/2011 |
| EP | 0742200 B1 | 7/1999 |
| WO | 8403281 A1 | 8/1984 |
| WO | 9938845 A1 | 8/1999 |
| WO | 9948492 A1 | 9/1999 |
| WO | 9965906 A1 | 12/1999 |
| WO | 0105390 A2 | 1/2001 |
| WO | 0119788 A2 | 3/2001 |
| WO | 0155121 A1 | 8/2001 |
| WO | 0185694 A2 | 11/2001 |
| WO | 02051410 A2 | 7/2002 |
| WO | 03007955 A2 | 1/2003 |
| WO | 03044016 A1 | 5/2003 |
| WO | 2004022060 A2 | 3/2004 |
| WO | 2004058709 A1 | 7/2004 |
| WO | 2004086865 A1 | 10/2004 |
| WO | 2004099192 A2 | 11/2004 |
| WO | 2004100947 A2 | 11/2004 |
| WO | 2005016922 A2 | 2/2005 |
| WO | 2005044797 A1 | 5/2005 |
| WO | 2005087217 A1 | 9/2005 |

(Continued)

OTHER PUBLICATIONS

International Search Report for International Application No. PCT/US2014/024509, Oct. 22, 2014 (6 pages).

Anthony, R. "West, solid state chemistry and its applications." (1984): p. 33-36.

Taylor, et al.; A Brain-Permeable Small Molecule Reduces Neuronal Cholesterol by Inhibiting Activity of Sirtuin 2 Deacetylase; ACS Chemical Biology, vol. 6, No. 6 Mar. 3, 2011, pp. 540-546.

Ermann et al.; Arylsulfonamide CB2 receptor agonists: SAR and optimization of CB2 selectivity; Bioorganic & Medicinal Chemistry Letters, vol. 18, No. 5, Mar. 1, 2008, pp. 1725-1729.

Lambeng, et al.; Arylsulfonamides as a new class of cannabinoid CB1 receptor ligands: Identification of a lead and initial SAR studies; Bioorganic & Medicinal Chemistry Letters, vol. 17, No. 1, Jan. 1, 2007, pp. 272-277.

(Continued)

*Primary Examiner* — Nizal Chandrakumar

(74) *Attorney, Agent, or Firm* — Lathrop & Gage LLP; Brian C. Trinque

(57) ABSTRACT

Provided herein are compounds useful for the treatment of HBV infection in man.

18 Claims, No Drawings

(56) References Cited

FOREIGN PATENT DOCUMENTS

| WO | 2005105785 A2 | 11/2005 |
|---|---|---|
| WO | 2005115374 A1 | 12/2005 |
| WO | 2006002133 A1 | 1/2006 |
| WO | 2006053109 A1 | 5/2006 |
| WO | 2006123257 A2 | 11/2006 |
| WO | 2006128129 A2 | 11/2006 |
| WO | 2006128172 A2 | 11/2006 |
| WO | 2007031791 A1 | 3/2007 |
| WO | 2008022171 A1 | 2/2008 |
| WO | 2008093614 A1 | 8/2008 |
| WO | 2008137794 A1 | 11/2008 |
| WO | 2009016088 A1 | 2/2009 |
| WO | 2009131065 A1 | 10/2009 |
| WO | 2010018113 A2 | 2/2010 |
| WO | 2010043592 A1 | 4/2010 |
| WO | 2010088000 A2 | 8/2010 |
| WO | 2010123139 A1 | 10/2010 |
| WO | 2011002635 A1 | 1/2011 |
| WO | 2011088015 A1 | 7/2011 |
| WO | 2011088561 A1 | 7/2011 |
| WO | 2011109237 A2 | 9/2011 |
| WO | 2011112191 A1 | 9/2011 |
| WO | 2011123609 A1 | 10/2011 |
| WO | 2011140324 A1 | 11/2011 |
| WO | 2011155898 A1 | 12/2011 |
| WO | 2012016133 A3 | 2/2012 |
| WO | 2012018635 A2 | 2/2012 |
| WO | 2012075235 A1 | 6/2012 |
| WO | 2012080050 A1 | 6/2012 |
| WO | 2012136834 A1 | 10/2012 |
| WO | 2013006394 A1 | 1/2013 |
| WO | 2013102655 A1 | 7/2013 |
| WO | 2013130703 A2 | 9/2013 |
| WO | 2013181584 A2 | 12/2013 |
| WO | 2014033167 A1 | 3/2014 |
| WO | 2014033170 A1 | 3/2014 |
| WO | 2014033176 A1 | 3/2014 |
| WO | 2014037480 A1 | 3/2014 |

OTHER PUBLICATIONS

El-Sharief, et al.; Synthesis of different types of chlorinated sulfonamides with expected insecticidal and bactericidal activities; Proceedings of the Indian National Science Academy, Part A: Physical Sciences, vol. 53, No. 1, 1987, pp. 179-188.

Mohamed, et al.; Synthesis of different types of chlorinated sulfonamides with expected insecticidal and antimicrobial activities; Acta Pharmaceutica Jugoslavica, vol. 36, No. 3, 1986, pp. 301-310.

International Search Report for Application No. PCT/US2012/071195 dated Dec. 21, 2012.

File History of U.S. Pat. No. 8,629,274.

Campagna, et al 'Sulfonamoylbenzamides Derivatives Inhibit the Assembly of Hepatitis B virus in Nucleocapsids'. 2013, vol. 87, No. 12, pp. 6931-6942.

U.S. Appl. No. 14/597,814, dated Jan. 15, 2015.
U.S. Appl. No. 14/517,606, dated Oct. 17, 2014.
U.S. Appl. No. 14/642,393, dated Mar. 9, 2015.
U.S. Appl. No. 14/511,964, dated Oct. 10, 2014.
U.S. Appl. No. 14/694,147, dated Apr. 23, 2015.

* cited by examiner

HEPATITIS B ANTIVIRAL AGENTS

RELATED APPLICATIONS

This application is a divisional of U.S. application Ser. No. 14/206,496, filed Mar. 12, 2014, which claims priority to U.S. Provisional Application Ser. No. 61/778,144, filed Mar. 12, 2013. The entire contents of these applications are herein incorporated by reference in their entireties.

BACKGROUND OF THE INVENTION

Chronic hepatitis B virus (HBV) infection is a significant global health problem, affecting over 5% of the world population (over 350 million people worldwide and 1.25 million individuals in the U.S.).

Despite the availability of a prophylactic HBV vaccine, the burden of chronic HBV infection continues to be a significant unmet worldwide medical problem, due to suboptimal treatment options and sustained rates of new infections in most parts of the developing world. Current treatments do not provide a cure and are limited to only two classes of agents (interferon and nucleoside analogues/inhibitors of the viral polymerase); drug resistance, low efficacy, and tolerability issues limit their impact. The low cure rates of HBV are attributed at least in part to the presence and persistence of covalently closed circular DNA (cccDNA) in the nucleus of infected hepatocytes. However, persistent suppression of HBV DNA slows liver disease progression and helps to prevent hepatocellular carcinoma. Current therapy goals for HBV-infected patients are directed to reducing serum HBV DNA to low or undetectable levels, and to ultimately reducing or preventing the development of cirrhosis and hepatocellular carcinoma.

There is a need in the art for novel therapeutic agents that treat, ameliorate or prevent HBV infection. Administration of these therapeutic agents to an HBV infected patient, either as monotherapy or in combination with other HBV treatments or ancillary treatments, will lead to significantly improved prognosis, diminished progression of the disease, and enhanced seroconversion rates.

SUMMARY OF THE INVENTION

Provided herein are compounds useful for the treatment of HBV infection in man.

Accordingly, in one aspect, provided herein is a compound of Formula I, II, III, IV, V, VI, VII, VIII, IX, X, XI, or XII, or pharmaceutically acceptable salts thereof. In one embodiment, provided herein is a pharmaceutical composition further comprising a compound of Formula I, II, III, IV, V, VI, VII, VIII, IX, X, XI, or XII, or a pharmaceutically acceptable salt thereof, at least one pharmaceutically acceptable carrier.

In one aspect, provided herein is a method of treating, eradicating, reducing, slowing, or inhibiting an HBV infection in an individual in need thereof, comprising administering to the individual a therapeutically effective amount of a compound of Formula I, II, III, IV, V, VI, VII, VIII, IX, X, XI, or XII, or a pharmaceutically acceptable salt thereof.

In another aspect, provided herein is a method of reducing the viral load associated with an HBV infection in an individual in need thereof, comprising administering to the individual a therapeutically effective amount of a compound of Formula I, II, III, IV, V, VI, VII, VIII, IX, X, XI, or XII, or a pharmaceutically acceptable salt thereof.

In yet another aspect, provided herein is a method of reducing reoccurrence of an HBV infection in an individual in need thereof, comprising administering to the individual a therapeutically effective amount of a compound of Formula I, II, III, IV, V, VI, VII, VIII, IX, X, XI, or XII, or a pharmaceutically acceptable salt thereof.

In another aspect, provided herein is a method of reducing an adverse physiological impact of an HBV infection in an individual in need thereof, comprising administering to the individual a therapeutically effective amount of a compound of Formula I, II, III, IV, V, VI, VII, VIII, IX, X, XI, or XII, or a pharmaceutically acceptable salt thereof.

In another aspect, provided herein is a method of inducing remission of hepatic injury from an HBV infection in an individual in need thereof, comprising administering to the individual a therapeutically effective amount of a compound of Formula I, II, III, IV, V, VI, VII, VIII, IX, X, XI, or XII, or a pharmaceutically acceptable salt thereof.

In still another aspect, provided herein is a method of reducing the physiological impact of long-term antiviral therapy for HBV infection in an individual in need thereof, comprising administering to the individual a therapeutically effective amount of Formula I, II, III, IV, V, VI, VII, VIII, IX, X, XI, or XII, or a pharmaceutically acceptable salt thereof.

In another aspect, provided herein is a method of prophylactically treating an HBV infection in an individual in need thereof, wherein the individual is afflicted with a latent HBV infection, comprising administering to the individual a therapeutically effective amount of a compound of Formula I, II, III, IV, V, VI, VII, VIII, IX, X, XI, or XII, or a pharmaceutically acceptable salt thereof.

In one embodiment of any of the methods described above, the methods further comprise administering to the individual at least one additional therapeutic agent selected from the group consisting of a HBV polymerase inhibitor, interferon, pegylated interferon, viral entry inhibitor, viral maturation inhibitor, literature-described capsid assembly modulator, reverse transcriptase inhibitor, a TLR-agonist, and agents of distinct or unknown mechanism, and a combination thereof.

In one embodiment, the pegylated interferon is pegylated interferon alpha (IFN-α) (e.g., PEGASYS®), pegylated interferon lambda (IFN-λ), or pegylated interferon gamma (IFN-γ).

In another embodiment, the reverse transcriptase inhibitor is at least one of Zidovudine, Didanosine, Zalcitabine, ddA, Stavudine, Lamivudine, Abacavir, Emtricitabine, Entecavir, Apricitabine, Atevirapine, ribavirin, acyclovir, famciclovir, valacyclovir, ganciclovir, valganciclovir, Tenofovir, Adefovir, PMPA, cidofovir, Efavirenz, Nevirapine, Delavirdine, or Etravirine.

In still another embodiment, the compound and the at least one additional therapeutic agent are co-formulated. In another embodiment, the compound and the at least one additional therapeutic agent are co-administered.

In one embodiment of the combination therapies, administering the compound of Formula I, II, III, IV, V, VI, VII, VIII, IX, X, XI, or XII, or a pharmaceutically acceptable salt thereof, allows for administering the at least one additional therapeutic agent at a lower dose or frequency as compared to the administering of the at least one additional therapeutic agent alone that is required to achieve similar results in prophylactically treating an HBV infection in an individual in need thereof.

In another embodiment of these methods, before administering the therapeutically effective amount of the compound of Formula I, II, III, IV, V, VI, VII, VIII, IX, X, XI, or XII, or a pharmaceutically acceptable salt thereof, the individual is known to be refractory to a compound selected from the group consisting of a HBV polymerase inhibitor, interferon, pegylated interferon, viral entry inhibitor, viral maturation inhibitor, distinct capsid assembly modulator, antiviral compounds of distinct or unknown mechanism, and combination thereof.

In still another embodiment, administering of the compound of Formula I, II, III, IV, V, VI, VII, VIII, IX, X, XI, or XII, or a pharmaceutically acceptable salt thereof, reduces viral load in the individual to a greater extent compared to the administering of a compound selected from the group consisting of a HBV polymerase inhibitor, interferon, pegylated interferon, viral entry inhibitor, viral maturation inhibitor, distinct capsid assembly modulator, antiviral compounds of distinct or unknown mechanism, and combination thereof.

In another embodiment, administering of the compound of Formula I, II, III, IV, V, VI, VII, VIII, IX, X, XI, or XII, or a pharmaceutically acceptable salt thereof, causes a lower incidence of viral mutation and/or viral resistance than the administering of a compound selected from the group consisting of a HBV polymerase inhibitor, interferon, pegylated interferon, viral entry inhibitor, viral maturation inhibitor, distinct capsid assembly modulator, antiviral compounds of distinct or unknown mechanism, and combination thereof.

DETAILED DESCRIPTION OF THE INVENTION

Provided herein are compounds that are useful in the treatment and prevention of HBV in man. In a non-limiting aspect, these compounds modulate and/or disrupt HBV assembly by interacting with HBV capsid to afford defective viral particles with greatly reduced virulence. The compounds of the invention have potent antiviral activity, exhibit favorable metabolic, tissue distribution, safety and pharmaceutical profiles, and are suitable for use in man.

The HBV capsid protein plays essential functions during the viral life cycle. HBV capsid/core proteins form metastable viral particles or protein shells that protect the viral genome during intercellular passage, and also play a central role in viral replication processes, including genome encapsidation, genome replication, and virion morphogenesis and egress. Capsid structures also respond to environmental cues to allow un-coating after viral entry. Consistently, proper capsid assembly has been found to be critical for viral infectivity.

The crucial function of HBV capsid proteins imposes stringent evolutionary constraints on the viral capsid protein sequence, leading to the observed low sequence variability and high conservation. Consistently, mutations in HBV capsid that disrupt its assembly are lethal, and mutations that perturb capsid stability severely attenuate viral replication. The more conserved a drug target is, the fewer replication-competent resistance mutations are acquired by patients. Indeed, natural mutations in HBV capsid for chronically infected patients accumulate in only four out of 183 residues in the full length protein. Thus, HBV capsid assembly inhibitors may elicit lower drug resistance emergence rates relative to existing HBV antivirals. Further, drug therapy that targets HBV capsid could be less prone to drug-resistant mutations when compared to drugs that target traditional NA enzyme active sites. Reports describing compounds that bind viral capsids and inhibit replication of HIV, rhinovirus and HBV provide strong pharmacological proof of concept for viral capsid proteins as antiviral drug targets.

In one aspect, the compounds of the invention are useful in HBV treatment by disrupting, accelerating, reducing, delaying and/or inhibiting normal viral capsid assembly and/or disassembly of immature or mature particles, thereby inducing aberrant capsid morphology and leading to antiviral effects such as disruption of virion assembly and/or disassembly, virion maturation, and/or virus egress. In one embodiment, a disruptor of capsid assembly interacts with mature or immature viral capsid to perturb the stability of the capsid, thus affecting assembly and/or disassembly. In another embodiment, a disruptor of capsid assembly perturbs protein folding and/or salt bridges required for stability, function and/or normal morphology of the viral capsid, thereby disrupting and/or accelerating capsid assembly and/or disassembly. In yet another embodiment, the compounds of the invention bind capsid and alter metabolism of cellular polyproteins and precursors, leading to abnormal accumulation of protein monomers and/or oligomers and/or abnormal particles, which causes cellular toxicity and death of infected cells. In another embodiment, the compounds of the invention cause failure of the formation of capsid of optimal stability, affecting efficient uncoating and/or disassembly of viruses (e.g., during infectivity).

In one embodiment, the compounds of the invention disrupt and/or accelerate capsid assembly and/or disassembly when the capsid protein is immature. In another embodiment, the compounds of the invention disrupt and/or accelerate capsid assembly and/or disassembly when the capsid protein is mature. In yet another embodiment, the compounds of the invention disrupt and/or accelerate capsid assembly and/or disassembly during vial infectivity. In yet another embodiment, the disruption and/or acceleration of capsid assembly and/or disassembly attenuates HBV viral infectivity and/or reduces viral load. In yet another embodiment, disruption, acceleration, inhibition, delay and/or reduction of capsid assembly and/or disassembly eradicates the virus from the host organism. In yet another embodiment, eradication of the HBV from a host advantageously obviates the need for chronic long-term therapy and/or reduces the duration of long-term therapy.

In one embodiment, the compounds described herein are suitable for monotherapy and are effective against natural or native HBV strains and against HBV strains resistant to currently known drugs. In another embodiment, the compounds described herein are suitable for use in combination therapy.

In another embodiment, the compounds of the invention can be used in methods of modulating (e.g., inhibit, disrupt or accelerate) the activity of HBV cccDNA. In yet another embodiment, the compounds of the invention can be used in methods of diminishing or preventing the formation of HBV cccDNA.

DEFINITIONS

As used herein, each of the following terms has the meaning associated with it in this section.

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry, and peptide chemistry are those well-known and commonly employed in the art.

As used herein, the articles "a" and "an" refer to one or to more than one (i.e. to at least one) of the grammatical object of the article. By way of example, "an element" means one element or more than one element. Furthermore, use of the term "including" as well as other forms, such as "include", "includes," and "included," is not limiting.

As used herein, the term "capsid assembly modulator" refers to a compound that disrupts and/or accelerates and/or inhibits and/or hinders and/or delays and or reduces and/or modifies normal capsid assembly (e.g., during maturation) and/or normal capsid disassembly (e.g., during infectivity) and/or perturbs capsid stability, thereby inducing aberrant capsid morphology and function. In one embodiment, a capsid assembly modulator accelerates capsid assembly and/or disassembly, thereby inducing aberrant capsid morphology. In another embodiment, a capsid assembly modulator interacts (e.g. binds at an active site, binds at an allosteric site, modifies and/or hinders folding and the like) with the major capsid assembly protein (CA), thereby disrupting capsid assembly and/or disassembly. In yet another embodiment, a capsid assembly modulator causes a perturbation in structure and/or function of CA (e.g., ability of CA to assemble, disassemble, bind to a substrate, fold into a suitable conformation, or the like), which attenuates viral infectivity and/or is lethal to the virus.

As used herein, the term "literature-described capsid assembly modulator" refers a capsid assembly modulator that is not a compound of the present invention.

As used herein, the term "treatment" or "treating," is defined as the application or administration of a therapeutic agent, i.e., a compound of the invention (alone or in combination with another pharmaceutical agent), to a patient, or application or administration of a therapeutic agent to an isolated tissue or cell line from a patient (e.g., for diagnosis or ex vivo applications), who has HBV infection, a symptom of HBV infection or the potential to develop HBV infection, with the purpose to cure, heal, alleviate, relieve, alter, remedy, ameliorate, improve or affect HBV infection, the symptoms of HBV infection or the potential to develop HBV infection. Such treatments may be specifically tailored or modified, based on knowledge obtained from the field of pharmacogenomics.

As used herein, the term "prevent" or "prevention" means no disorder or disease development if none had occurred, or no further disorder or disease development if there had already been development of the disorder or disease. Also considered is the ability of one to prevent some or all of the symptoms associated with the disorder or disease.

As used herein, the term "patient," "individual" or "subject" refers to a human or a non-human mammal. Non-human mammals include, for example, livestock and pets, such as ovine, bovine, porcine, canine, feline and murine mammals. Preferably, the patient, subject or individual is human.

As used herein, the terms "effective amount," "pharmaceutically effective amount" and "therapeutically effective amount" refer to a nontoxic but sufficient amount of an agent to provide the desired biological result. That result may be reduction and/or alleviation of the signs, symptoms, or causes of a disease, or any other desired alteration of a biological system. An appropriate therapeutic amount in any individual case may be determined by one of ordinary skill in the art using routine experimentation.

As used herein, the term "pharmaceutically acceptable" refers to a material, such as a carrier or diluent, which does not abrogate the biological activity or properties of the compound, and is relatively non-toxic, i.e., the material may be administered to an individual without causing undesirable biological effects or interacting in a deleterious manner with any of the components of the composition in which it is contained.

As used herein, the language "pharmaceutically acceptable salt" refers to a salt of the administered compounds prepared from pharmaceutically acceptable non-toxic acids, including inorganic acids, organic acids, solvates, hydrates, or clathrates thereof. Examples of such inorganic acids are hydrochloric, hydrobromic, hydroiodic, nitric, sulfuric, phosphoric, acetic, hexafluorophosphoric, citric, gluconic, benzoic, propionic, butyric, sulfosalicylic, maleic, lauric, malic, fumaric, succinic, tartaric, amsonic, pamoic, p-toluenesulfonic, and mesylic. Appropriate organic acids may be selected, for example, from aliphatic, aromatic, carboxylic and sulfonic classes of organic acids, examples of which are formic, acetic, propionic, succinic, camphorsulfonic, citric, fumaric, gluconic, isethionic, lactic, malic, mucic, tartaric, para-toluenesulfonic, glycolic, glucuronic, maleic, furoic, glutamic, benzoic, anthranilic, salicylic, phenylacetic, mandelic, embonic (pamoic), methanesulfonic, ethanesulfonic, pantothenic, benzenesulfonic (besylate), stearic, sulfanilic, alginic, galacturonic, and the like. Furthermore, pharmaceutically acceptable salts include, by way of non-limiting example, alkaline earth metal salts (e.g., calcium or magnesium), alkali metal salts (e.g., sodium-dependent or potassium), and ammonium salts.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations.

As used herein, "pharmaceutically acceptable carrier" also includes any and all coatings, antibacterial and antifungal agents, and absorption delaying agents, and the like that are compatible with the activity of the compound useful within the invention, and are physiologically acceptable to the patient. Supplementary active compounds may also be incorporated into the compositions. The "pharmaceutically acceptable carrier" may further include a pharmaceutically acceptable salt of the compound useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, Pa.), which is incorporated herein by reference.

As used herein, the term "composition" or "pharmaceutical composition" refers to a mixture of at least one compound useful within the invention with a pharmaceutically acceptable carrier. The pharmaceutical composition facilitates administration of the compound to a patient or subject. Multiple techniques of administering a compound exist in the art including, but not limited to, intravenous, oral, aerosol, parenteral, ophthalmic, pulmonary and topical administration.

As used herein, the term "alkyl," by itself or as part of another substituent means, unless otherwise stated, a straight or branched chain hydrocarbon having the number of carbon atoms designated (i.e., $C_{1-6}$ means one to six carbon atoms) and includes straight, branched chain, or cyclic substituent groups. Examples include methyl, ethyl, propyl, isopropyl, butyl, isobutyl, tert-butyl, pentyl, neopentyl, hexyl, and cyclopropylmethyl. Most preferred is ($C_1$-$C_6$)alkyl, particularly ethyl, methyl, isopropyl, isobutyl, n-pentyl, n-hexyl and cyclopropylmethyl.

As used herein, the term "substituted alkyl" means alkyl as defined above, substituted by one, two or three substituents selected from the group consisting of halogen, —OH, alkoxy, —NH$_2$, —N(CH$_3$)$_2$, —C(=O)OH, trifluoromethyl, —C≡N, —C(=O)O(C$_1$-C$_4$)alkyl, —C(=O)NH$_2$, —SO$_2$NH$_2$, —C(=NH)NH$_2$, and —NO$_2$, preferably containing one or two substituents selected from halogen, —OH, alkoxy, —NH$_2$, trifluoromethyl, —N(CH$_3$)$_2$, and —C(=O) OH, more preferably selected from halogen, alkoxy and —OH. Examples of substituted alkyls include, but are not limited to, 2,2-difluoropropyl, 2-carboxycyclopentyl and 3-chloropropyl.

As used herein, the term "heteroalkyl" by itself or in combination with another term means, unless otherwise stated, a stable straight or branched chain alkyl group consisting of the stated number of carbon atoms and one or two heteroatoms selected from the group consisting of O, N, and S, and wherein the nitrogen and sulfur atoms may be optionally oxidized and the nitrogen heteroatom may be optionally quaternized. The heteroatom(s) may be placed at any position of the heteroalkyl group, including between the rest of the heteroalkyl group and the fragment to which it is attached, as well as attached to the most distal carbon atom in the heteroalkyl group. Examples include: —O—CH$_2$—CH$_2$—CH$_3$, —CH$_2$—CH$_2$—CH$_2$—OH, —CH$_2$—CH$_2$—NH—CH$_3$, —CH$_2$—S—CH$_2$—CH$_3$, and —CH$_2$CH$_2$—S(=O)—CH$_3$. Up to two heteroatoms may be consecutive, such as, for example, —CH$_2$—NH—OCH$_3$, or —CH$_2$—CH$_2$—S—S—CH$_3$. Preferred heteroalkyl groups have 1-10 carbons.

As used herein, the term "alkoxy" employed alone or in combination with other terms means, unless otherwise stated, an alkyl group having the designated number of carbon atoms, as defined above, connected to the rest of the molecule via an oxygen atom, such as, for example, methoxy, ethoxy, 1-propoxy, 2-propoxy (isopropoxy) and the higher homologs and isomers. Preferred are ($C_1$-$C_3$)alkoxy, particularly ethoxy and methoxy.

As used herein, the term "halo" or "halogen" alone or as part of another substituent means, unless otherwise stated, a fluorine, chlorine, bromine, or iodine atom, preferably, fluorine, chlorine, or bromine, more preferably, fluorine or chlorine.

As used herein, the term "cycloalkyl" or "carbocyclyl" refers to a mono cyclic or polycyclic non-aromatic radical, wherein each of the atoms forming the ring (i.e., skeletal atoms) is a carbon atom. In one embodiment, the cycloalkyl group is saturated or partially unsaturated. In another embodiment, the cycloalkyl group is fused with an aromatic ring. Cycloalkyl groups include groups having from 3 to 10 ring atoms. Illustrative examples of cycloalkyl groups include, but are not limited to, the following moieties:

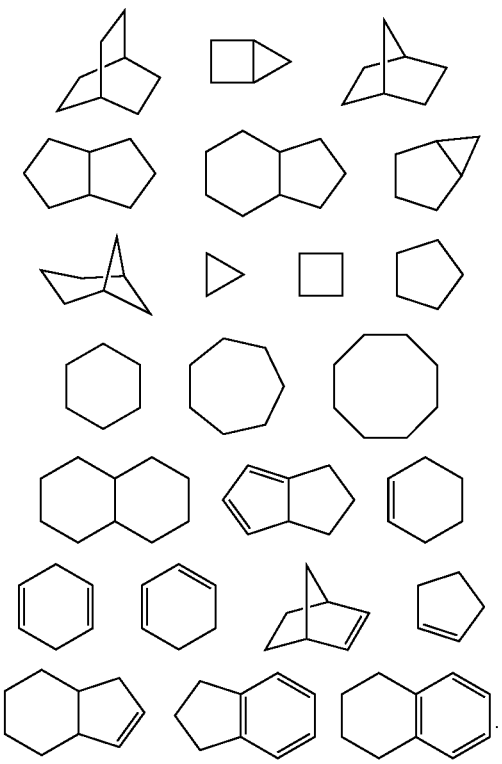

Monocyclic cycloalkyls include, but are not limited to, cyclopropyl, cyclobutyl, cyclopentyl, cyclohexyl, cycloheptyl, and cyclooctyl. Dicyclic cycloalkyls include, but are not limited to, tetrahydronaphthyl, indanyl, and tetrahydropentalene. Polycyclic cycloalkyls include adamantine and norbornane. The term cycloalkyl includes "unsaturated nonaromatic carbocyclyl" or "nonaromatic unsaturated carbocyclyl" groups, both of which refer to a nonaromatic carbocycle as defined herein, which contains at least one carbon carbon double bond or one carbon carbon triple bond.

As used herein, the term "heterocycloalkyl" or "heterocyclyl" refers to a heteroalicyclic group containing one to four ring heteroatoms each selected from O, S and N. In one embodiment, each heterocycloalkyl group has from 4 to 10 atoms in its ring system, with the proviso that the ring of said group does not contain two adjacent O or S atoms. In another embodiment, the heterocycloalkyl group is fused with an aromatic ring. In one embodiment, the nitrogen and sulfur heteroatoms may be optionally oxidized, and the nitrogen atom may be optionally quaternized. The heterocyclic system may be attached, unless otherwise stated, at any heteroatom or carbon atom that affords a stable structure. A heterocycle may be aromatic or non-aromatic in nature. In one embodiment, the heterocycle is a heteroaryl.

An example of a 3-membered heterocycloalkyl group includes, and is not limited to, aziridine. Examples of 4-membered heterocycloalkyl groups include, and are not limited to, azetidine and a beta lactam. Examples of 5-membered heterocycloalkyl groups include, and are not limited to, pyrrolidine, oxazolidine and thiazolidinedione. Examples of 6-membered heterocycloalkyl groups include, and are not limited to, piperidine, morpholine and piperazine. Other non-limiting examples of heterocycloalkyl groups are:

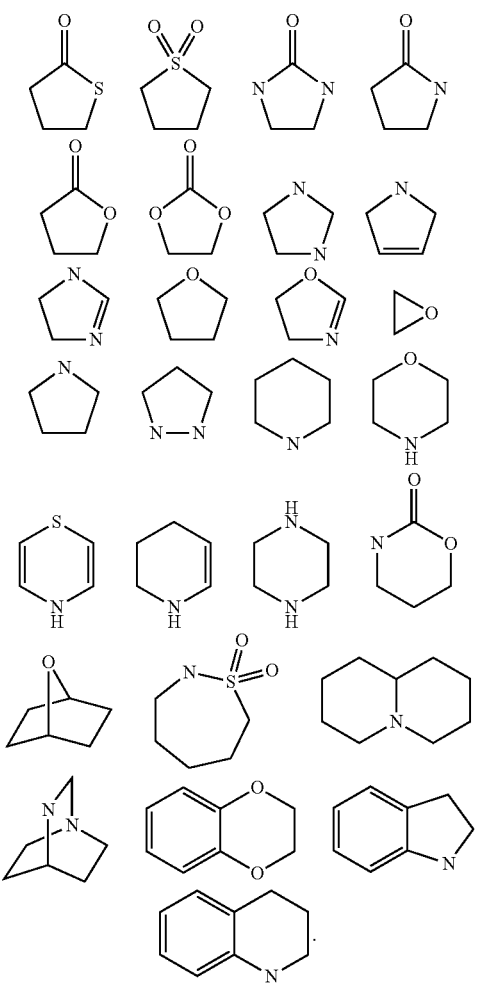

Examples of non-aromatic heterocycles include monocyclic groups such as aziridine, oxirane, thiirane, azetidine, oxetane, thietane, pyrrolidine, pyrroline, pyrazolidine, imidazoline, dioxolane, sulfolane, 2,3-dihydrofuran, 2,5-dihydrofuran, tetrahydrofuran, thiophane, piperidine, 1,2,3,6-tetrahydropyridine, 1,4-dihydropyridine, piperazine, morpholine, thiomorpholine, pyran, 2,3-dihydropyran, tetrahydropyran, 1,4-dioxane, 1,3-dioxane, homopiperazine, homopiperidine, 1,3-dioxepane, 4,7-dihydro-1,3-dioxepin, and hexamethyleneoxide.

As used herein, the term "aromatic" refers to a carbocycle or heterocycle with one or more polyunsaturated rings and having aromatic character, i.e., having (4n+2) delocalized π (pi) electrons, where n is an integer.

As used herein, the term "aryl," employed alone or in combination with other terms, means, unless otherwise stated, a carbocyclic aromatic system containing one or more rings (typically one, two or three rings), wherein such rings may be attached together in a pendent manner, such as a biphenyl, or may be fused, such as naphthalene. Examples of aryl groups include phenyl, anthracyl, and naphthyl. Preferred examples are phenyl and naphthyl, most preferred is phenyl.

Examples of polycyclic heterocycles and heteroaryls include indolyl (particularly 3-, 4-, 5-, 6- and 7-indolyl), indolinyl, quinolyl, tetrahydroquinolyl, isoquinolyl (particularly 1- and 5-isoquinolyl), 1,2,3,4-tetrahydroisoquinolyl, cinnolinyl, quinoxalinyl (particularly 2- and 5-quinoxalinyl), quinazolinyl, phthalazinyl, 1,8-naphthyridinyl, 1,4-benzodioxanyl, coumarin, dihydrocoumarin, 1,5-naphthyridinyl, benzofuryl (particularly 3-, 4-, 5-, 6- and 7-benzofuryl), 2,3-dihydrobenzofuryl, 1,2-benzisoxazolyl, benzothienyl (particularly 3-, 4-, 5-, 6-, and 7-benzothienyl), benzoxazolyl, benzothiazolyl (particularly 2-benzothiazolyl and 5-benzothiazolyl), purinyl, benzimidazolyl (particularly 2-benzimidazolyl), benzotriazolyl, thioxanthinyl, carbazolyl, carbolinyl, acridinyl, pyrrolizidinyl, and quinolizidinyl.

As used herein, the term "substituted" means that an atom or group of atoms has replaced hydrogen as the substituent attached to another group. The term "substituted" further refers to any level of substitution, namely mono-, di-, tri-, tetra-, or penta-substitution, where such substitution is permitted. The substituents are independently selected, and substitution may be at any chemically accessible position. In one embodiment, the substituents vary in number between one and four. In another embodiment, the substituents vary in number between one and three. In yet another embodiment, the substituents vary in number between one and two.

Compounds of the Invention

The present invention relates to the discovery of compounds that are useful in the treatment and prevention of HBV in man. In one aspect, the compounds of the invention are useful in HBV treatment by disrupting, accelerating, reducing delaying and/or inhibiting normal viral capsid assembly and/or disassembly of immature or mature particles, thereby inducing aberrant capsid morphology and leading to antiviral effects such as disruption of virion assembly and/or disassembly and/or virion maturation, and/or virus egress.

The capsid assembly disruptors disclosed herein may be used as monotherapy and/or in novel cross-class combination regimens for treating HBV infection in man. Combination therapy with drugs exhibiting different mechanism of action (MOA) that act at different steps in the virus life cycle may deliver greater efficacy due to additive or synergistic antiviral effects. Clinically evaluated HIV treatment regimens have shown that combination therapy improves the efficacy of viral load reduction, and dramatically reduces emergence of antiviral resistance. Combination therapy for the treatment of Hepatitis C (HCV) virus infection has also resulted in significant improvement in sustained antiviral response and eradication rates. Thus, use of the HBV capsid assembly inhibitors of the present invention in combination with, for example, NA drugs, is likely to deliver a more profound antiviral effect and greater disease eradication rates than current standards of care.

Capsid assembly plays a central role in HBV genome replication. HBV polymerase binds pre-genomic HBV RNA (pgRNA), and pgRNA encapsidation must occur prior to HBV DNA synthesis. Moreover, it is well established that nuclear accumulation of the cccDNA replication intermediate, which is responsible for maintenance of chronic HBV replication in the presence of nucleoside suppressive therapy, requires the capsid for shuttling HBV DNA to the nuclei. Therefore, the HBV capsid assembly disruptors of the invention have the potential to increase HBV eradication rates through synergistic or additive suppression of viral genome replication and to further reduce accumulation of cccDNA when used alone or in combination with existing nucleoside drugs. The capsid assembly disruptors of the present invention may also alter normal core protein degradation, potentially leading to altered MHC-1 antigen presentation, which may in turn increase seroconversion/eradication rates through immuno-stimulatory activity, more effectively clearing infected cells.

In one aspect, drug resistance poses a major threat to current therapies for chronic HBV infection, and cross-class combination therapy is a proven strategy for delaying emergence of drug resistance strains. The capsid assembly disruptors of the present invention can, when administered alone or in combination with other HBV therapy, offer enhanced drug resistant profiles and improved management of chronic HBV.

The compounds useful within the invention may be synthesized using techniques well-known in the art of organic synthesis. The starting materials and intermediates required for the synthesis may be obtained from commercial sources or synthesized according to methods known to those skilled in the art.

In one aspect, the compound of the invention is a compound of Formula I,

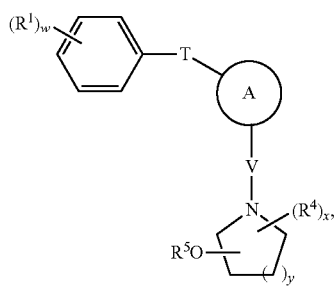

(I)

or a pharmaceutically acceptable salt thereof, wherein:
Ring A is selected from:

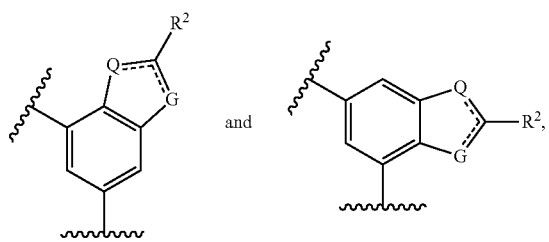

and wherein:
G is N, and Q is $CH_2$ or $NR^3$, or
G is $NR^3$, and Q is CH or N, or
G is CH, and Q is $NR^3$, or
G is $CH_2$, and Q is N; and ⸺ represents a single or double bond;
T is selected from —C(O)—, —NH(C(O))— and —S(O)$_2$—;
V is selected from —C(O)— and —S(O)$_2$—;
$R^1$ in each occurrence is independently selected from halo, —CN, $C_{1-6}$alkyl, —O$C_{1-6}$ alkyl, and —NO$_2$, wherein the $C_{1-6}$alkyl is optionally substituted with one to three halo;
$R^2$ in each occurrence is independently selected from hydrogen, halo, and $C_{1-6}$alkyl;
$R^3$ is selected from H and $C_{1-6}$ alkyl;
$R^4$ in each occurrence is independently selected from halo, $C_{1-6}$alkyl, monocyclic 5 to 7-membered carbocyclyl, monocyclic 5 to 7-membered heterocyclyl, —OR$^{4a}$, —SR$^{4a}$, and —N(R$^{4a}$)$_2$, wherein the $C_{1-6}$alkyl, monocyclic 5 to 7-membered carbocyclyl, and monocyclic 5 to 7-membered heterocyclyl are optionally substituted with one or more R$^{40}$;

$R^{4a}$ in each occurrence is independently selected from H, $C_{1-6}$alkyl, monocyclic 5 to 7-membered carbocyclyl, and monocyclic 5 to 7-membered heterocyclyl, wherein said $C_{1-6}$alkyl, monocyclic 5 to 7-membered carbocyclyl, and monocyclic 5 to 7-membered heterocyclyl, are optionally and independently substituted with one or more R$^{40}$;

$R^5$ is selected from H and $C_{1-6}$alkyl;

$R^{40}$ in each occurrence is independently selected from halo, —CN, $C_{1-6}$alkyl, monocyclic 5 to 7-membered carbocyclyl, monocyclic 5 to 7-membered heterocyclyl, —OR$^{40a}$, —SR$^{40a}$, —N(R$^{40a}$)$_2$, —NO$_2$, —C(O)R$^{40b}$, and —C(O)$_2$R$^{40a}$;

$R^{40a}$ in each occurrence is independently selected from H, $C_{1-6}$alkyl, monocyclic 5 to 7-membered carbocyclyl, and monocyclic 5 to 7-membered heterocyclyl;

$R^{40b}$ in each occurrence is independently selected from $C_{1-6}$alkyl, monocyclic 5 to 7-membered carbocyclyl, and monocyclic 5 to 7-membered heterocyclyl;

w is 0, 1, 2, or 3;
x is 0 or 1; and
y is 0, 1, or 2.

In one embodiment of Formula I, $R^4$ in each occurrence is independently selected from halo, $C_{1-6}$alkyl, and —OR$^{4a}$, wherein the $C_{1-6}$alkyl is optionally substituted with one or more halo; and R$^{4a}$ in each occurrence is independently selected from H or $C_{1-6}$alkyl.

In one embodiment, the compound of Formula I is a compound of Formula II:

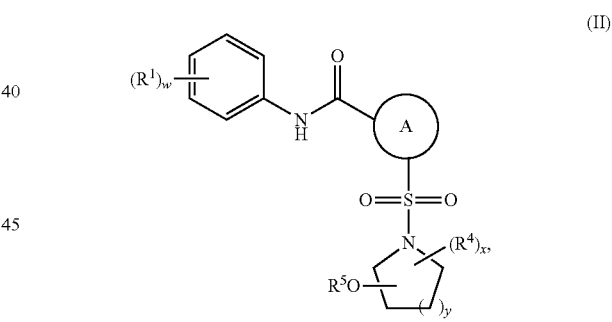

(II)

or a pharmaceutically acceptable salt thereof, wherein:
Ring A is selected from:

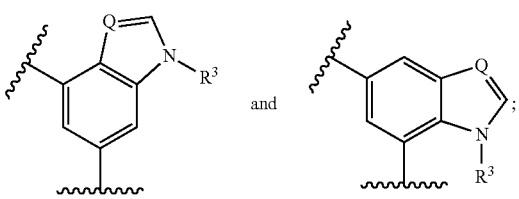

and and

Q is CH or N, or

Ring A is

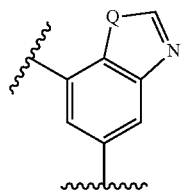

and Q is CH$_2$ or NR$^3$.

In one embodiment of Formulas I or II, R$^1$ is halo.

In another embodiment of Formulas I or II, R$^1$ in each occurrence is independently selected from fluorine and chlorine, R$^3$ in each occurrence is independently selected from H and methyl, R$^4$ is selected from H and methyl, and w is 0, 2, or 3.

In another embodiment of Formulas I or II, R$^1$ in each occurrence is independently selected from fluorine and chlorine, R$^3$ is H, R$^4$ is H, and w is 0, 2, or 3.

In one embodiment, the compound of Formulas I or II is a compound of Formula III:

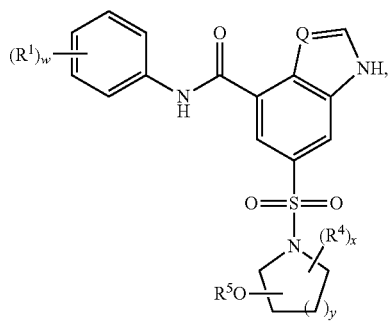

(III)

or a pharmaceutically acceptable salt thereof.

In one embodiment of Formula III, R$^1$ in each occurrence is independently selected from fluorine and chlorine, R$^4$ is selected from H and methyl, and w is 0, 2, or 3. In another embodiment of Formula III, R$^4$ in each occurrence is independently selected from halo, C$_{1-6}$alkyl, and —OR$^{4a}$, wherein the C$_{1-6}$alkyl is optionally substituted with one or more halo; and R$^{4a}$ in each occurrence is independently selected from H or C$_{1-6}$alkyl.

In another embodiment, the compound of Formula III is a compound of Formula IV:

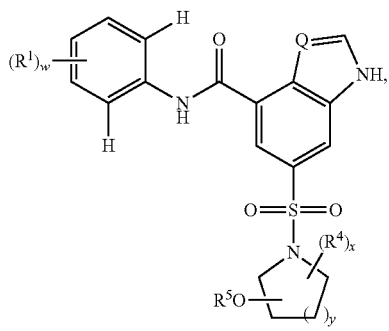

(IV)

or a pharmaceutically acceptable salt thereof.

In one embodiment of Formula IV, R$^1$ in each occurrence is independently selected from fluorine and chlorine, R$^4$ is selected from H and methyl, and w is 0, 2, or 3. In another embodiment of Formula IV, R$^4$ in each occurrence is independently selected from halo, C$_{1-6}$alkyl, and —OR$^{4a}$, wherein the C$_{1-6}$alkyl is optionally substituted with one or more halo; and R$^{4a}$ in each occurrence is independently selected from H or C$_{1-6}$alkyl.

In one embodiment, the compound of Formulas I or II is a compound of Formula V:

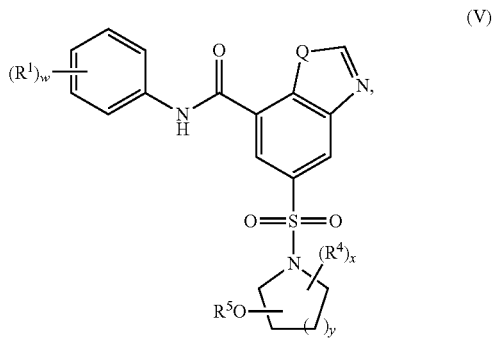

(V)

or a pharmaceutically acceptable salt thereof.

In one embodiment of Formula V, R$^1$ in each occurrence is independently selected from fluorine and chlorine, R$^3$ in each occurrence is independently selected from H and methyl, R$^4$ is selected from H and methyl, and w is 0, 2, or 3. In another embodiment of Formula V, R$^4$ in each occurrence is independently selected from halo, C$_{1-6}$alkyl, and —OR$^{4a}$, wherein the C$_{1-6}$alkyl is optionally substituted with one or more halo; and R$^{4a}$ in each occurrence is independently selected from H or C$_{1-6}$alkyl.

In another embodiment, the compound of Formula V is a compound of Formula VI:

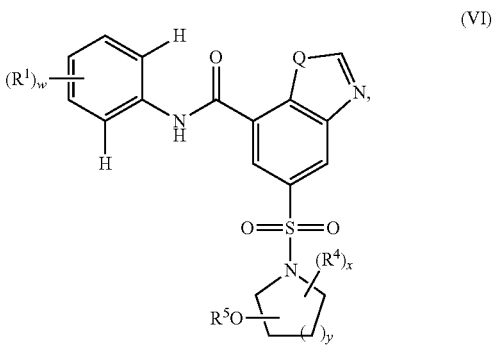

(VI)

or a pharmaceutically acceptable salt thereof.

In one embodiment of Formula VI, R$^1$ in each occurrence is independently selected from fluorine and chlorine, R$^3$ in each occurrence is independently selected from H and methyl, R$^4$ is selected from H and methyl, and w is 0, 2, or 3. In another embodiment of Formula VI, R$^4$ in each occurrence is independently selected from halo, C$_{1-6}$alkyl, and —OR$^{4a}$, wherein the C$_{1-6}$alkyl is optionally substituted with one or more halo; and R$^{4a}$ in each occurrence is independently selected from H or C$_{1-6}$alkyl.

In yet another embodiment, the compound of Formulas I or II is a compound of Formula VII:

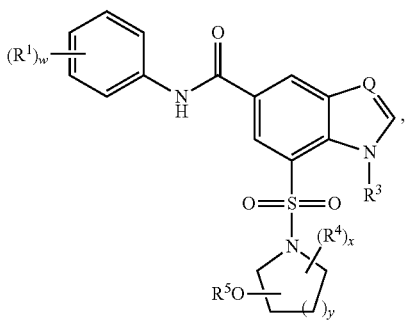

(VII)

or a pharmaceutically acceptable salt thereof.

In one embodiment of Formula VII, $R^1$ in each occurrence is independently selected from fluorine and chlorine, $R^3$ in each occurrence is independently selected from H and methyl, $R^4$ is selected from H and methyl, and w is 0, 2, or 3. In another embodiment of Formula VII, $R^4$ in each occurrence is independently selected from halo, $C_{1-6}$alkyl, and $-OR^{4a}$, wherein the $C_{1-6}$alkyl is optionally substituted with one or more halo; and $R^{4a}$ in each occurrence is independently selected from H or $C_{1-6}$alkyl.

In another embodiment, the compound of Formula VII is a compound of Formula VIII:

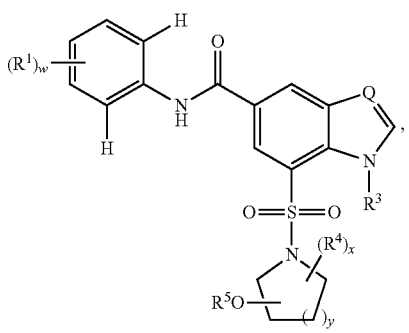

(VIII)

or a pharmaceutically acceptable salt thereof.

In one embodiment of Formula VIII, $R^1$ in each occurrence is independently selected from fluorine and chlorine, $R^3$ in each occurrence is independently selected from H and methyl, $R^4$ is selected from H and methyl, and w is 0, 2, or 3. In another embodiment of Formula VIII, $R^4$ in each occurrence is independently selected from halo, $C_{1-6}$alkyl, and $-OR^{4a}$, wherein the $C_{1-6}$alkyl is optionally substituted with one or more halo; and $R^{4a}$ in each occurrence is independently selected from H or $C_{1-6}$alkyl.

In another aspect, the compound of the invention is a compound of Formula IX:

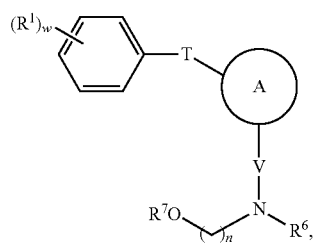

(IX)

or a pharmaceutically acceptable salt thereof, wherein:
Ring A is selected from:

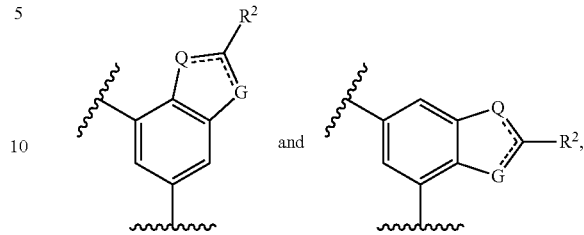

wherein:
G is N, and Q is $CH_2$ or $NR^3$, or
G is $NR^3$, and Q is CH or N, or
G is CH, and Q is $NR^3$, or
G is $CH_2$, and Q is N; and
═══ represents a single or double bond;

T is selected from $-C(O)-$, $-NH(C(O))-$, and $-S(O)_2-$;

V is selected from $-C(O)-$ and $-S(O)_2-$;

$R^1$ in each occurrence is independently selected from halo, $-CN$, $C_{1-6}$alkyl, $-OC_{1-6}$alkyl, and $-NO_2$, wherein the $C_{1-6}$alkyl is optionally substituted with one to three halo;

$R^2$ in each occurrence is independently selected from hydrogen, halo, and $C_{1-6}$alkyl;

$R^3$ is selected from H and $C_{1-6}$alkyl;

$R^6$ is H or $C_{1-6}$ alkyl;

$R^7$ is H or $C_{1-6}$ alkyl;

n is 1, 2, 3, 4, 5, or 6; and w is 0, 1, 2, or 3.

In one embodiment, the compound of Formula IX is a compound of Formula X:

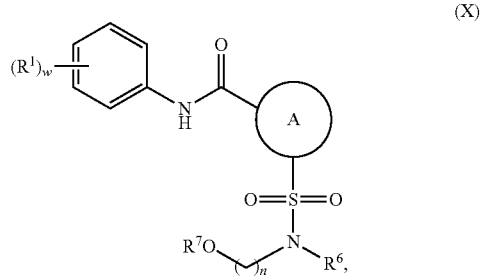

(X)

or a pharmaceutically acceptable salt thereof,
wherein:
Ring A is selected from:

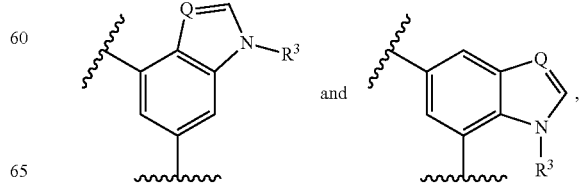

and Q is CH or N, or
Ring A is

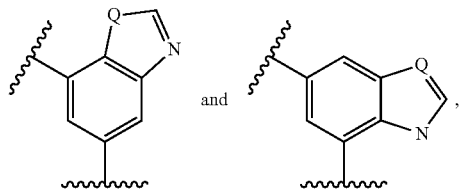

and Q is CH$_2$ or NR$^3$.

In a further aspect, the compound of the invention is a compound of Formula XI:

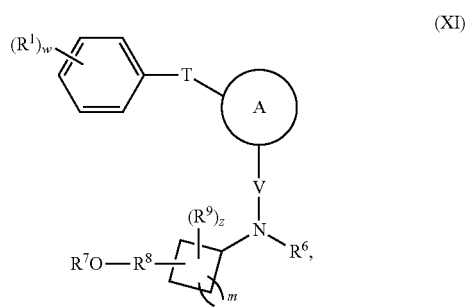

(XI)

or a pharmaceutically acceptable salt thereof, wherein:
Ring A is selected from:

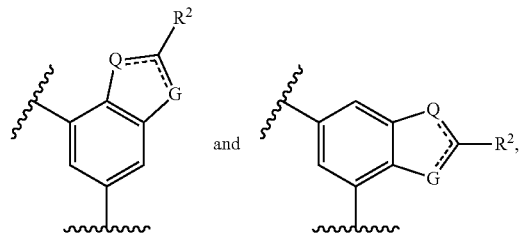

wherein:
G is N, and Q is CH$_2$ or NR$^3$, or
G is NR$^3$, and Q is CH or N, or
G is CH, and Q is NR$^3$, or
G is CH$_2$, and Q is N; and
---- represents a single or double bond;
T is selected from —C(O)—, —NH(C(O))—, and —S(O)$_2$—;
V is selected from —C(O)— and —S(O)$_2$—;
R$^1$ in each occurrence is independently selected from halo, —CN, C$_{1-6}$alkyl, —OC$_{1-6}$alkyl, and —NO$_2$, wherein the C$_{1-6}$alkyl is optionally substituted with one to three halo;
R$^2$ in each occurrence is independently selected from hydrogen, halo, and C$_{1-6}$alkyl;
R$^3$ is selected from H and C$_{1-6}$alkyl;
R$^6$ is H or C$_{1-6}$ alkyl;
R$^7$ is H or C$_{1-6}$ alkyl, and R$^8$ is a bond or C$_1$-C$_3$ alkylene, wherein the C$_1$-C$_3$ alkylene is optionally substituted with 1-3 substituents selected from R$^{10}$, or
—R$^8$—OR$^7$ is absent;
R$^9$ in each occurrence is independently OH, halo, C$_1$-C$_6$ alkyl, C$_1$-C$_6$ alkyl-OH, C$_1$-C$_6$ fluoroalkyl, C$_1$-C$_6$ heteroalkyl, C$_3$-C$_{10}$ cycloalkyl, a C$_3$-C$_{10}$ heterocycloalkyl, aryl, heteroaryl, —C$_1$-C$_4$ alkyl-(C$_3$-C$_{10}$ cycloalkyl), —C$_1$-C$_4$ alkyl-(C$_3$-C$_{10}$ heterocycloalkyl), —C$_1$-C$_4$ alkyl-(aryl), or —C$_1$-C$_4$ alkyl-(hetero aryl), and wherein the alkyl, heteroalkyl, cycloalkyl, heterocycloalkyl, aryl or heteroaryl ring is optionally substituted with 1-5 substituents selected from R$^{10}$;

R$^{10}$ is independently selected at each occurrence from the group consisting of halo, —CN, —NO$_2$, —C$_1$-C$_6$ alkyl, —C$_1$-C$_6$ alkoxy, —C$_1$-C$_6$ fluoroalkyl, —C$_1$-C$_6$ heteroalkyl, and C(O)—C$_1$-C$_6$ alkyl;
w is 0, 1, 2, or 3;
m is 0, 1, 2, or 3; and
z is 0, 1, 2, or 3.

In one embodiment, the compound of Formula XI is a compound of Formula XII:

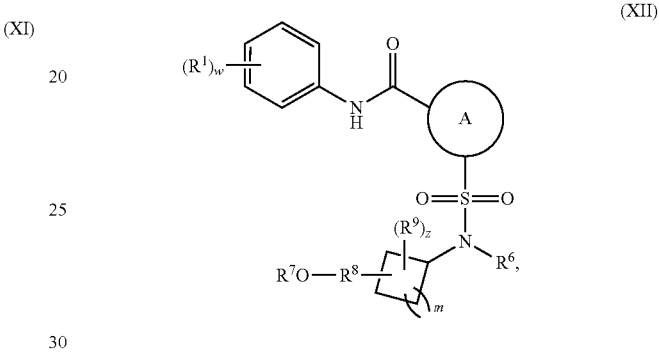

(XII)

or a pharmaceutically acceptable salt thereof, wherein:
Ring A is selected from:

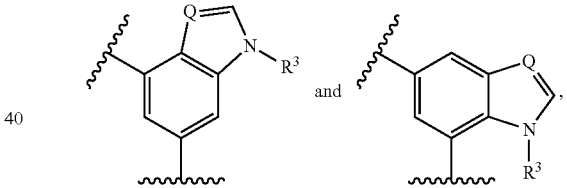

and Q is CH or N, or
Ring A is

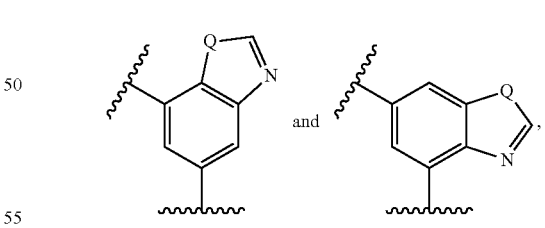

and Q is CH$_2$ or NR$^3$.

It will be appreciated that the description of the present invention herein should be construed in congruity with the laws and principals of chemical bonding. In some instances it will be necessary to remove a hydrogen atom in order to accommodate a substituent at any given location.

It is noted for the generic structures described herein that rings that are substituted by two or more variables (R groups, RO groups, etc.) can indicate, for example, either vicinal (e.g., compound 1290) or geminal (e.g., compound 1302) substitution patterns.

Preferred embodiments of Formulas I-VI, including pharmaceutically acceptable salts thereof, as well as enantiomers, stereoisomers, rotamers, tautomers, diastereomers, atropisomers or racemates thereof, and are shown below in Table 1 and are also considered to be "compounds of the invention."

TABLE 1

| Structure | Compound ID | 1H NMR | MS (M + H)+ |
|---|---|---|---|
| [structure] | 948 | | |
| [structure] | 949 | 1H NMR (400 MHz, MeOD)-d4) 8.11 (s, 1H), 8.09-8.05 (m, 1H), 7.92 (s, 1H), 7.76-7.63 (m, 2H), 7.33 (t, J = 8.8 Hz, 1H), 7.04 (s, 1H), 3.71-3.62 (m, 1H), 3.51-3.41 (m, 2H), 2.91-2.73 (m, 2H), 2.01-1.91 (m, 2H), 1.67-1.57 (m, 2H). | 452 |
| [structure] | 950 | | |

TABLE 1-continued
| Structure | Compound ID | ¹H NMR | MS (M + H)⁺ |
|---|---|---|---|
| 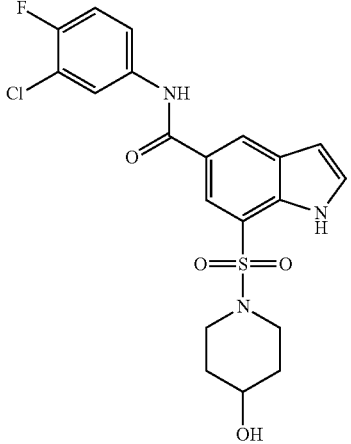 [SMILES: O=C(Nc1ccc(F)c(Cl)c1)c1cc(S(=O)(=O)N2CCC(O)CC2)c2[nH]ccc2c1] | 951 | | |
| 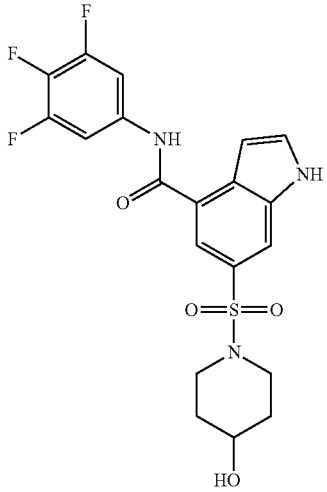 [SMILES: O=C(Nc1cc(F)c(F)c(F)c1)c1cc(S(=O)(=O)N2CCC(O)CC2)cc2[nH]ccc12] | 1287 | | 454 |
| 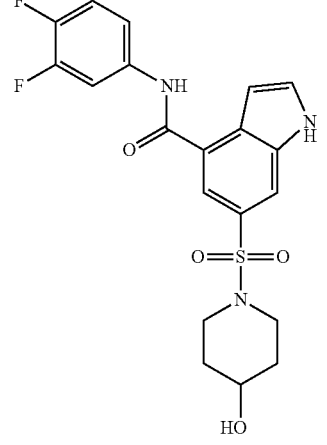 | 1288 | | 436 |

TABLE 1-continued

| Structure | Compound ID | ¹H NMR | MS (M + H)⁺ |
|---|---|---|---|
| 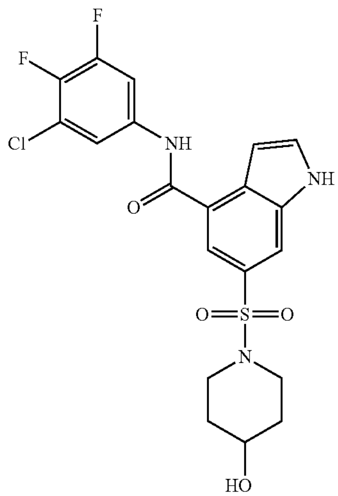 [SMILES: O=C(Nc1cc(F)c(F)c(Cl)c1)c1cc(S(=O)(=O)N2CCC(O)CC2)cc2[nH]ccc12] | 1289 | | |
| 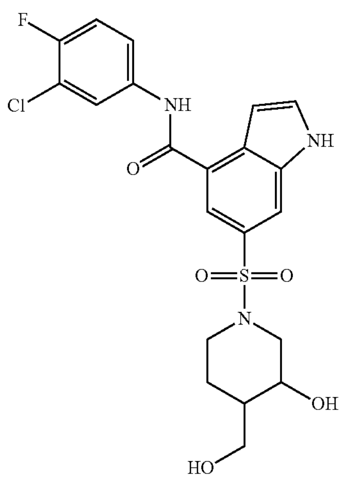 [SMILES: O=C(Nc1ccc(F)c(Cl)c1)c1cc(S(=O)(=O)N2CCC(CO)C(O)C2)cc2[nH]ccc12] | 1290 | | 482 |
| 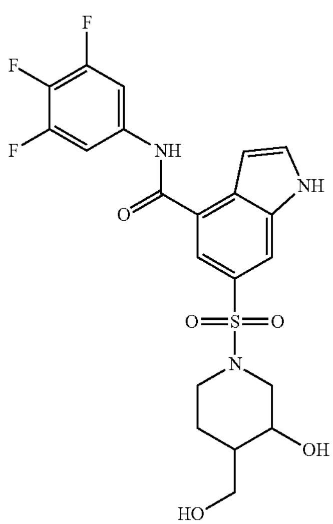 [SMILES: O=C(Nc1cc(F)c(F)c(F)c1)c1cc(S(=O)(=O)N2CCC(CO)C(O)C2)cc2[nH]ccc12] | 1291 | 1H NMR (400 MHz, MeOD-d4) 8.08 (s, 1H), 7.89 (s, 1H), 7.71-7.65 (m, 3H), 7.00 (s, 1H), 4.01-3.77 (m, 3H), 3.62-3.31 (m, 2H), 2.57-2.26 (m, 2H), 1.81-1.45 (m, 3H) | 484 |

TABLE 1-continued

| Structure | Compound ID | ¹H NMR | MS (M + H)⁺ |
|---|---|---|---|
| 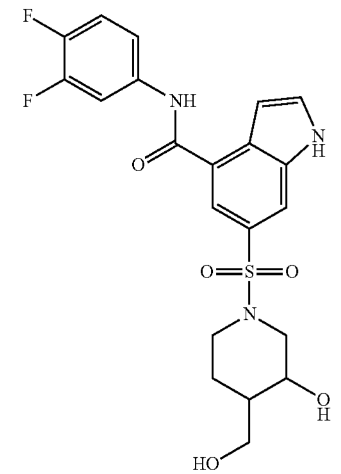 [SMILES: O=C(Nc1ccc(F)c(F)c1)c1cc(S(=O)(=O)N2CCC(CO)C(O)C2)cc2[nH]ccc12] | 1292 | 1H NMR (400 MHz, MeOD-d4) 8.07 (s, 1H), 7.97-7.75 (m, 2H), 7.70 (s, 1H), 7.51-7.26 (m, 2H), 6.99 (s, 1H), 4.02-3.76 (m, 3H), 3.61-3.30 (m, 2H), 2.51-2.30 (m, 2H), 1.83-1.42 (m, 3H) | 466 |
| 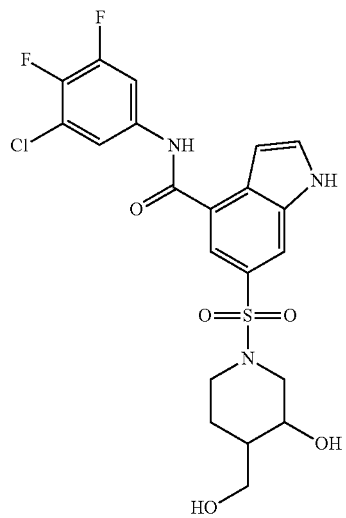 [SMILES: O=C(Nc1cc(F)c(F)c(Cl)c1)c1cc(S(=O)(=O)N2CCC(CO)C(O)C2)cc2[nH]ccc12] | 1293 | | |
| 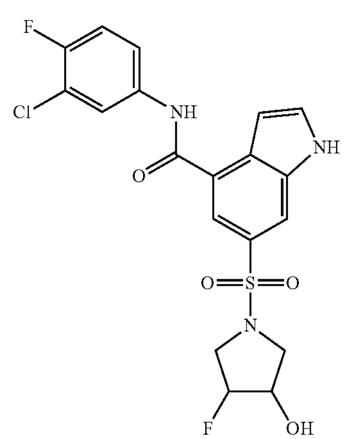 [SMILES: O=C(Nc1ccc(F)c(Cl)c1)c1cc(S(=O)(=O)N2CC(O)C(F)C2)cc2[nH]ccc12] | 1294 | | 456 |

TABLE 1-continued

| Structure | Compound ID | ¹H NMR | MS (M + H)⁺ |
|---|---|---|---|
| 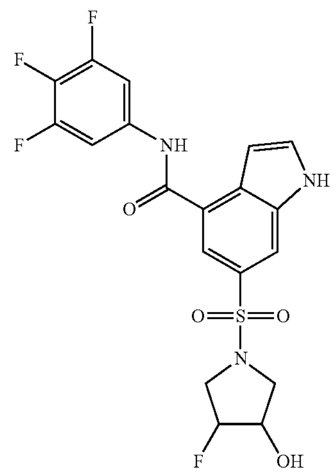 [SMILES: O=C(Nc1cc(F)c(F)c(F)c1)c1cc(S(=O)(=O)N2CC(O)C(F)C2)cc2[nH]ccc12] | 1295 | 1H NMR (400 MHz, MeOD-d4) 8.14 (s, 1H), 7.96 (s, 1H), 7.72-7.63 (m, 3H), 6.99 (s, 1H), 4.91-4.77 (m, 1H), 4.31-4.17 (m, 1H), 3.72-3.39 (m, 4H). | 458 |
| 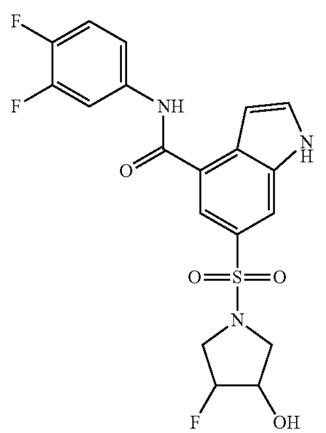 [SMILES: O=C(Nc1ccc(F)c(F)c1)c1cc(S(=O)(=O)N2CC(O)C(F)C2)cc2[nH]ccc12] | 1296 | 1H NMR (400 MHz, MeOD-d4) 8.14 (s, 1H), 7.95 (s, 1H), 7.93-7.81 (m, 1H), 7.69 (s, 1H), 7.57-7.39 (m, 1H), 7.31-7.22 (m, 1H), 6.99 (s, 1H), 4.93-4.77 (m, 1H), 4.33-4.19 (m, 1H), 3.71-3.35 (m, 4H). | 440 |
| 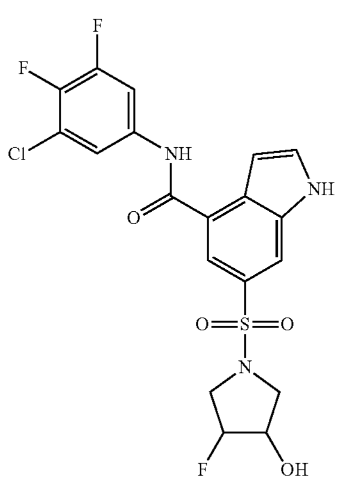 [SMILES: O=C(Nc1cc(F)c(F)c(Cl)c1)c1cc(S(=O)(=O)N2CC(O)C(F)C2)cc2[nH]ccc12] | 1297 | | |

TABLE 1-continued

| Structure | Compound ID | ¹H NMR | MS (M + H)⁺ |
|---|---|---|---|
| 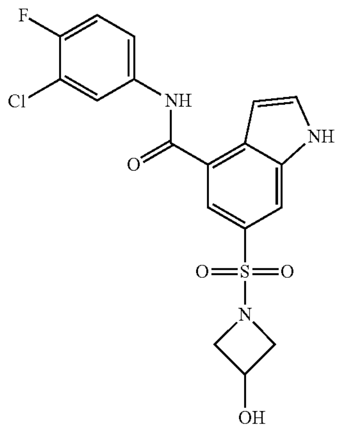 [SMILES: O=C(Nc1ccc(F)c(Cl)c1)c1cc(S(=O)(=O)N2CC(O)C2)cc2[nH]ccc12] | 1298 | | 424 |
| 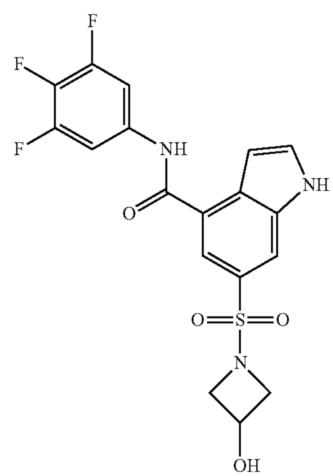 [SMILES: O=C(Nc1cc(F)c(F)c(F)c1)c1cc(S(=O)(=O)N2CC(O)C2)cc2[nH]ccc12] | 1299 | | 426 |
| 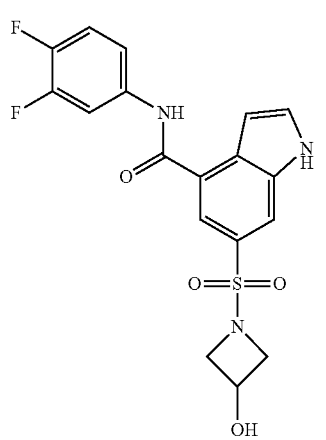 [SMILES: O=C(Nc1ccc(F)c(F)c1)c1cc(S(=O)(=O)N2CC(O)C2)cc2[nH]ccc12] | 1300 | 1H NMR (400 MHz, MeOD-d4) 8.13 (s, 1H), 7.97-7.83 (m, 2H), 7.73 (s, 1H), 7.51-7.42 (m, 1H), 7.37-7.26 (m, 1H), 7.02 (s, 1H), 4.48-4.31 (m, 1H) 4.05-3.92 (m, 2H), 3.63-3.51 (m, 2H). | 408 |

TABLE 1-continued

| Structure | Compound ID | ¹H NMR | MS (M + H)⁺ |
|---|---|---|---|
| 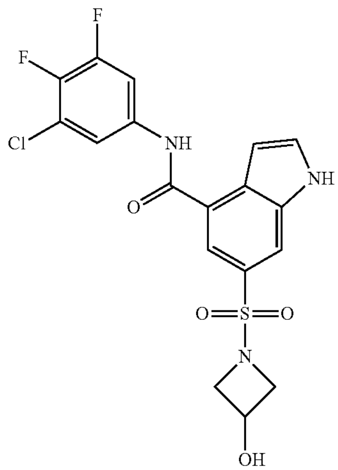 [SMILES: O=C(Nc1cc(F)c(F)c(Cl)c1)c1cc(S(=O)(=O)N2CC(O)C2)cc2[nH]ccc12] | 1301 | | |
| 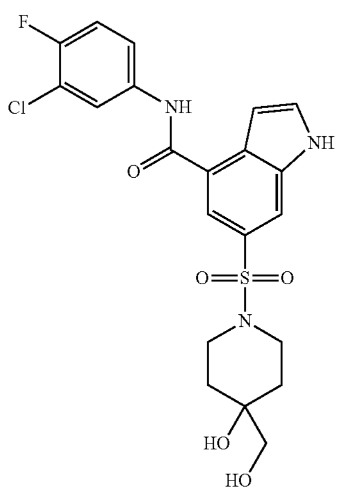 [SMILES: O=C(Nc1ccc(F)c(Cl)c1)c1cc(S(=O)(=O)N2CCC(O)(CO)CC2)cc2[nH]ccc12] | 1302 | | 482 |
| 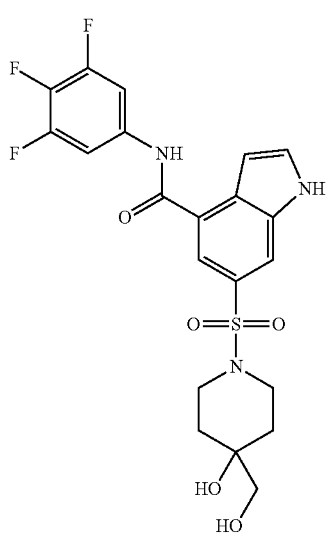 [SMILES: O=C(Nc1cc(F)c(F)c(F)c1)c1cc(S(=O)(=O)N2CCC(O)(CO)CC2)cc2[nH]ccc12] | 1303 | | 484 |

TABLE 1-continued

| Structure | Compound ID | ¹H NMR | MS (M + H)⁺ |
|---|---|---|---|
| 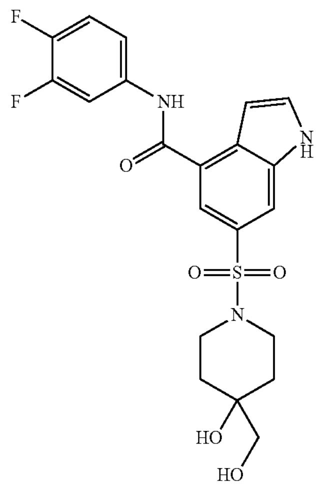 [SMILES: O=C(Nc1ccc(F)c(F)c1)c1cc(S(=O)(=O)N2CCC(O)(CO)CC2)cc2[nH]ccc12] | 1304 | 1H NMR (400 MHz, MeOD-d4) 8.07 (s, 1H), 7.95-7.82 (m, 2H), 7.70 (s, 1H), 7.52-7.26 (m, 2H), 6.99 (s, 1H), 3.66-3.59 (m, 2H), 3.33 (s, 2H), 2.74-2.61 (m, 2H), 1.83-1.51 (m, 4H) | 466 |
| 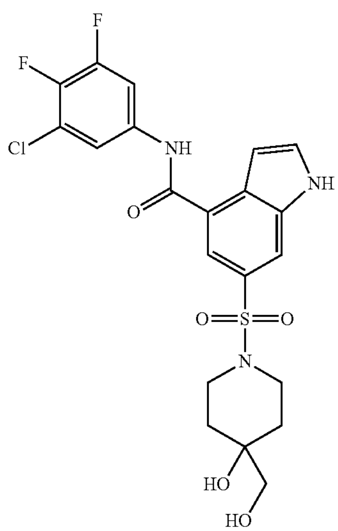 [SMILES: O=C(Nc1cc(F)c(F)c(Cl)c1)c1cc(S(=O)(=O)N2CCC(O)(CO)CC2)cc2[nH]ccc12] | 1305 | | |
| 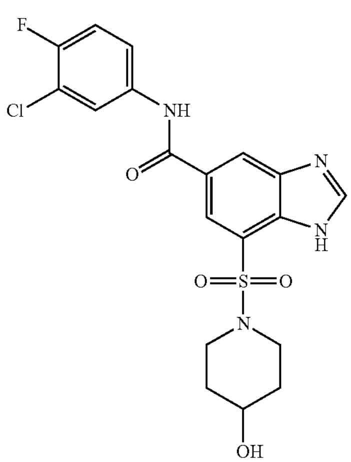 [SMILES: O=C(Nc1ccc(F)c(Cl)c1)c1cc(S(=O)(=O)N2CCC(O)CC2)c2[nH]cnc2c1] | 1472 | | 453 |

TABLE 1-continued

| Structure | Compound ID | ¹H NMR | MS (M + H)⁺ |
|---|---|---|---|
| 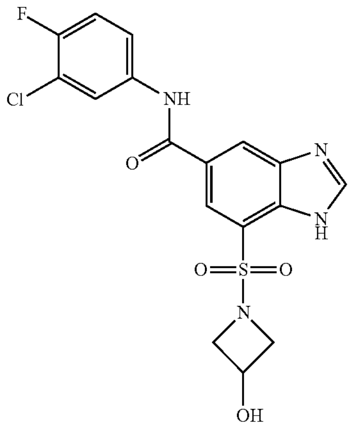 [SMILES: O=C(Nc1ccc(F)c(Cl)c1)c1cc(S(=O)(=O)N2CC(O)C2)c2[nH]cnc2c1] | 1473 | | |
| 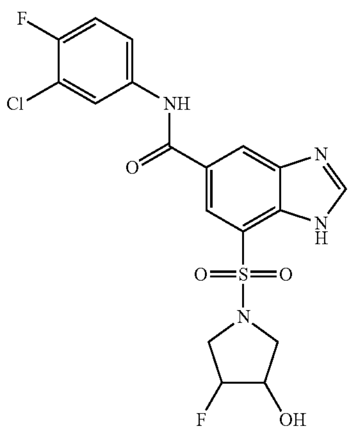 [SMILES: O=C(Nc1ccc(F)c(Cl)c1)c1cc(S(=O)(=O)N2CC(O)C(F)C2)c2[nH]cnc2c1] | 1474 | | |
| 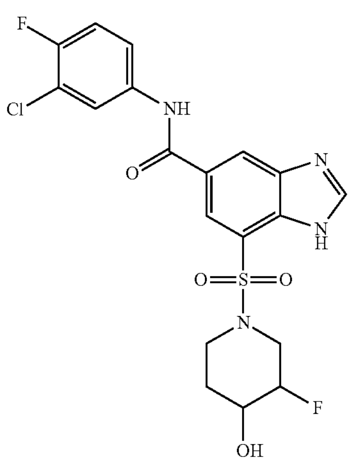 [SMILES: O=C(Nc1ccc(F)c(Cl)c1)c1cc(S(=O)(=O)N2CCC(O)C(F)C2)c2[nH]cnc2c1] | 1475 | | |

TABLE 1-continued
| Structure | Compound ID | ¹H NMR | MS (M + H)⁺ |
|---|---|---|---|
| 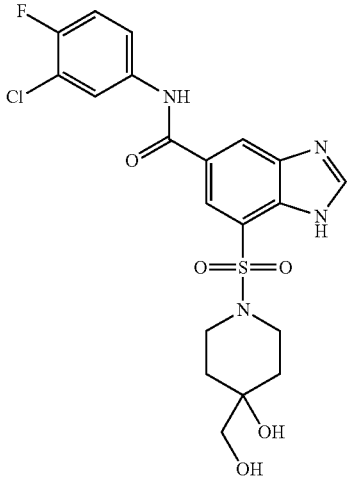 [SMILES: O=C(Nc1ccc(F)c(Cl)c1)c1cc(S(=O)(=O)N2CCC(O)(CO)CC2)c2[nH]cnc2c1] | 1476 | | |
| 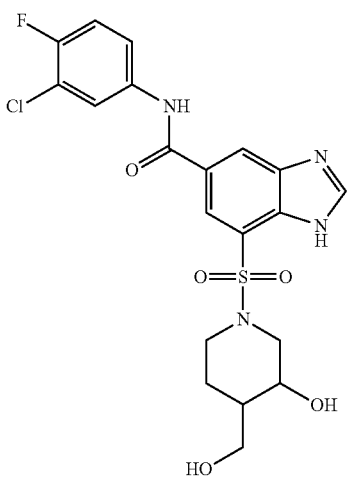 [SMILES: O=C(Nc1ccc(F)c(Cl)c1)c1cc(S(=O)(=O)N2CCC(CO)C(O)C2)c2[nH]cnc2c1] | 1477 | | |
| 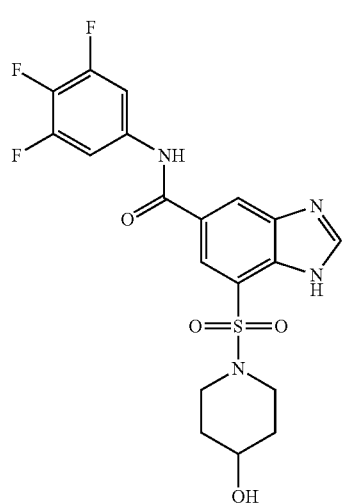 [SMILES: O=C(Nc1cc(F)c(F)c(F)c1)c1cc(S(=O)(=O)N2CCC(O)CC2)c2[nH]cnc2c1] | 1478 | | |

TABLE 1-continued

| Structure | Compound ID | ¹H NMR | MS (M + H)⁺ |
|---|---|---|---|
| 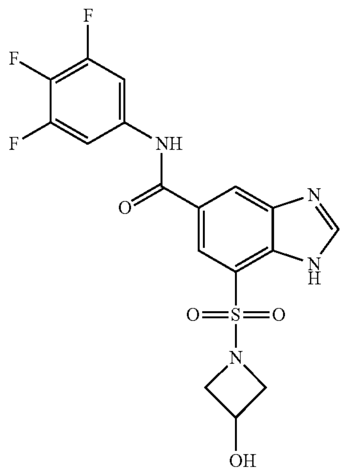 [SMILES: O=C(Nc1cc(F)c(F)c(F)c1)c1cc(S(=O)(=O)N2CC(O)C2)c2[nH]cnc2c1] | 1479 |  |  |
| 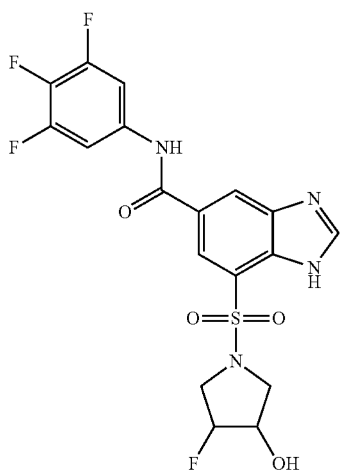 [SMILES: O=C(Nc1cc(F)c(F)c(F)c1)c1cc(S(=O)(=O)N2CC(O)C(F)C2)c2[nH]cnc2c1] | 1480 |  |  |
| 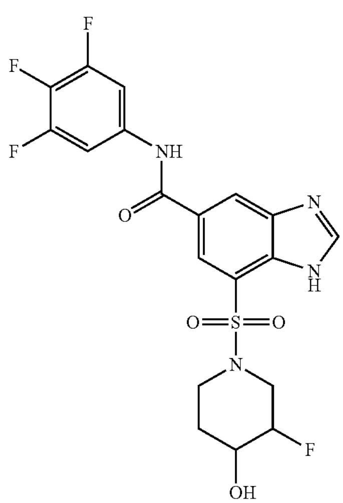 [SMILES: O=C(Nc1cc(F)c(F)c(F)c1)c1cc(S(=O)(=O)N2CCC(O)C(F)C2)c2[nH]cnc2c1] | 1481 |  |  |

TABLE 1-continued

| Structure | Compound ID | ¹H NMR | MS (M + H)⁺ |
|---|---|---|---|
| 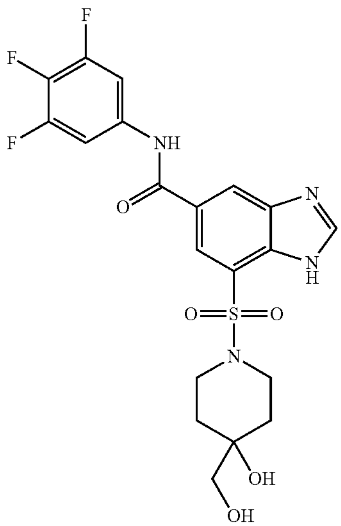 [SMILES: O=C(Nc1cc(F)c(F)c(F)c1)c1cc(S(=O)(=O)N2CCC(O)(CO)CC2)c2[nH]cnc2c1] | 1482 | | |
| 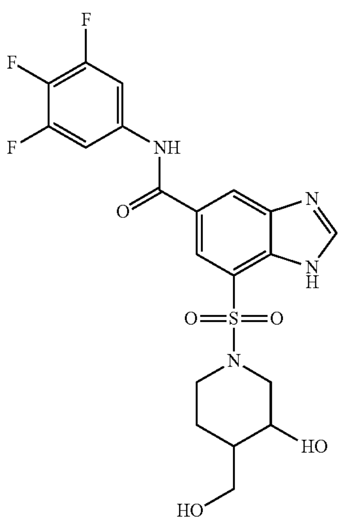 [SMILES: O=C(Nc1cc(F)c(F)c(F)c1)c1cc(S(=O)(=O)N2CCC(CO)C(O)C2)c2[nH]cnc2c1] | 1483 | | |
| 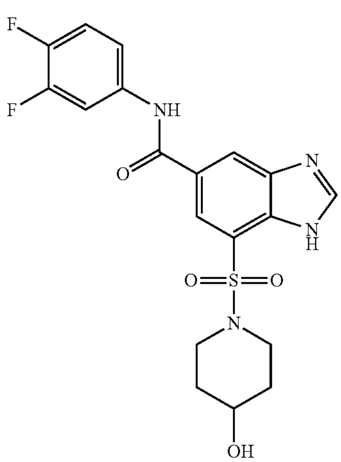 [SMILES: O=C(Nc1ccc(F)c(F)c1)c1cc(S(=O)(=O)N2CCC(O)CC2)c2[nH]cnc2c1] | 1484 | | |

TABLE 1-continued

| Structure | Compound ID | ¹H NMR | MS (M + H)⁺ |
|---|---|---|---|
| 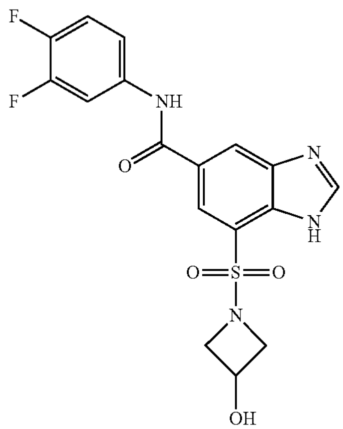 [SMILES: O=C(Nc1ccc(F)c(F)c1)c1cc(S(=O)(=O)N2CC(O)C2)c2[nH]cnc2c1] | 1485 | | |
| 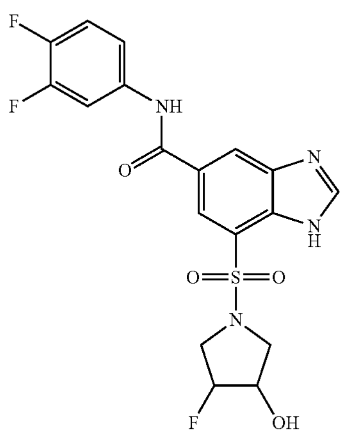 [SMILES: O=C(Nc1ccc(F)c(F)c1)c1cc(S(=O)(=O)N2CC(O)C(F)C2)c2[nH]cnc2c1] | 1486 | | |
| 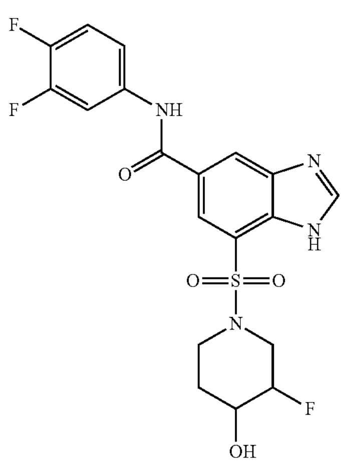 [SMILES: O=C(Nc1ccc(F)c(F)c1)c1cc(S(=O)(=O)N2CCC(O)C(F)C2)c2[nH]cnc2c1] | 1487 | | |

TABLE 1-continued

| Structure | Compound ID | $^1$H NMR | MS $(M + H)^+$ |
|---|---|---|---|
| 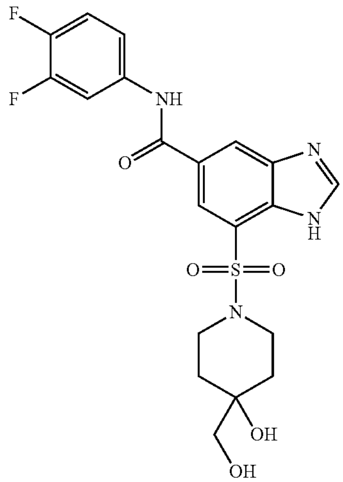 [SMILES: O=C(Nc1ccc(F)c(F)c1)c1cc(S(=O)(=O)N2CCC(O)(CO)CC2)c2[nH]cnc2c1] | 1488 | | |
| 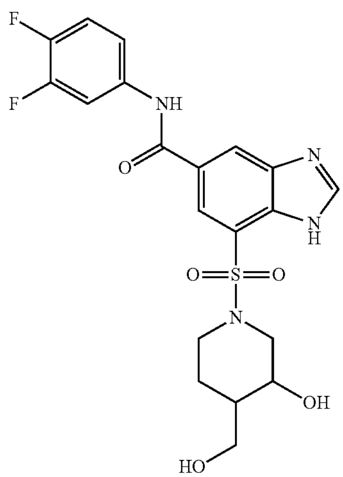 [SMILES: O=C(Nc1ccc(F)c(F)c1)c1cc(S(=O)(=O)N2CCC(CO)C(O)C2)c2[nH]cnc2c1] | 1489 | | |
| 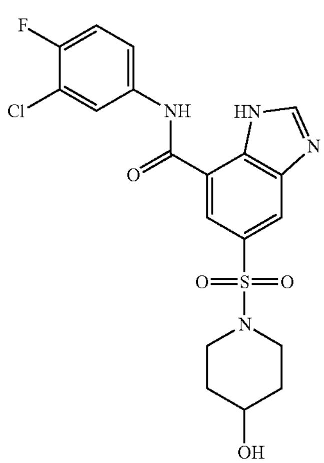 [SMILES: O=C(Nc1ccc(F)c(Cl)c1)c1cc(S(=O)(=O)N2CCC(O)CC2)cc2nc[nH]c12] | 1490 | | |

TABLE 1-continued

| Structure | Compound ID | ¹H NMR | MS (M + H)⁺ |
|---|---|---|---|
| 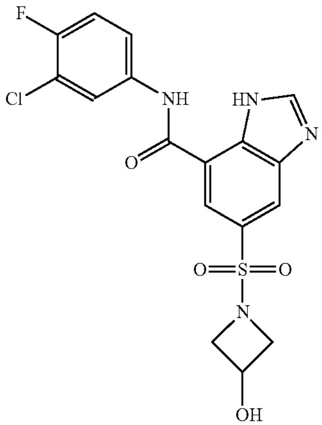 [SMILES: O=C(Nc1ccc(F)c(Cl)c1)c1cc(S(=O)(=O)N2CC(O)C2)cc2nc[nH]c12] | 1491 | | |
| 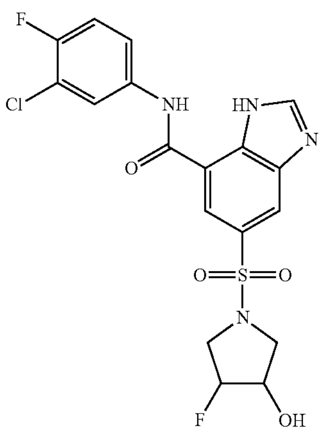 [SMILES: O=C(Nc1ccc(F)c(Cl)c1)c1cc(S(=O)(=O)N2CC(O)C(F)C2)cc2nc[nH]c12] | 1492 | | |
| 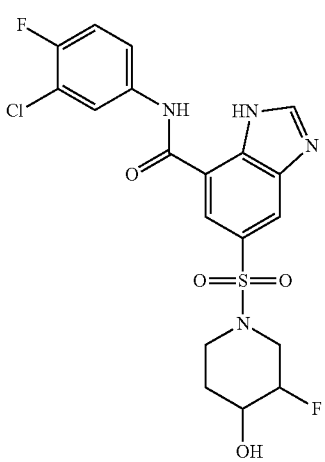 [SMILES: O=C(Nc1ccc(F)c(Cl)c1)c1cc(S(=O)(=O)N2CCC(O)C(F)C2)cc2nc[nH]c12] | 1493 | | |

TABLE 1-continued
| Structure | Compound ID | ¹H NMR | MS (M + H)⁺ |
|---|---|---|---|
| 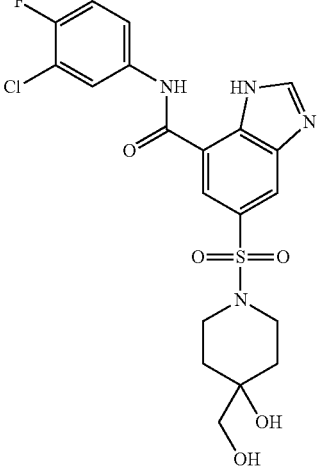 | 1494 | | |
| 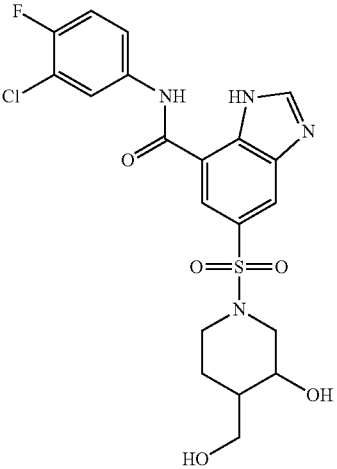 [SMILES: O=C(Nc1ccc(F)c(Cl)c1)c1cc(S(=O)(=O)N2CCC(CO)C(O)C2)cc2nc[nH]c12] | 1495 | | |
| 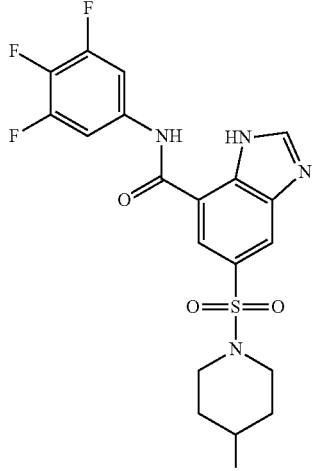 | 1496 | | |

TABLE 1-continued
| Structure | Compound ID | ¹H NMR | MS (M + H)⁺ |
|---|---|---|---|
| 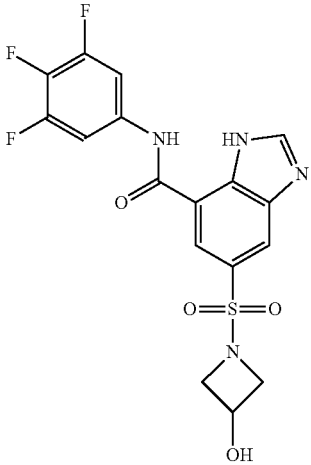 | 1497 | | |
| 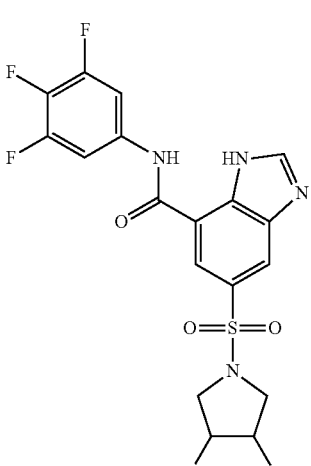 | 1498 | | |
| 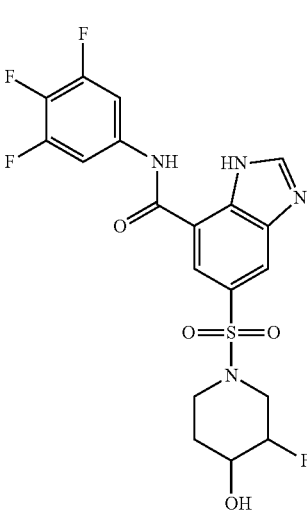 [SMILES: O=C(Nc1cc(F)c(F)c(F)c1)c1cc(S(=O)(=O)N2CCC(O)CC2)cc2nc[nH]c12] | 1499 | | |

TABLE 1-continued
| Structure | Compound ID | ¹H NMR | MS (M + H)⁺ |
|---|---|---|---|
| 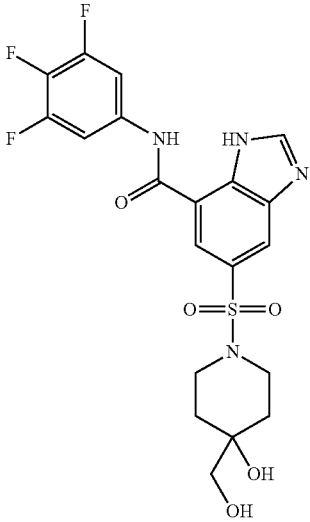 [SMILES: O=C(Nc1cc(F)c(F)c(F)c1)c1cc(S(=O)(=O)N2CCC(O)(CO)CC2)cc2nc[nH]c12] | 1500 | | |
| 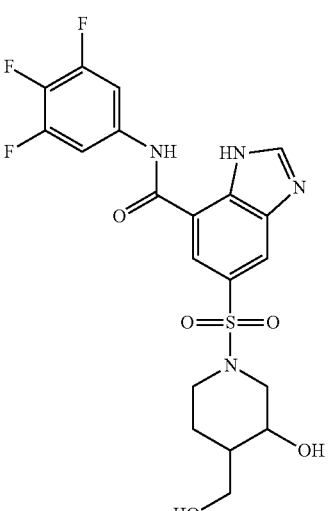 | 1501 | | |
| 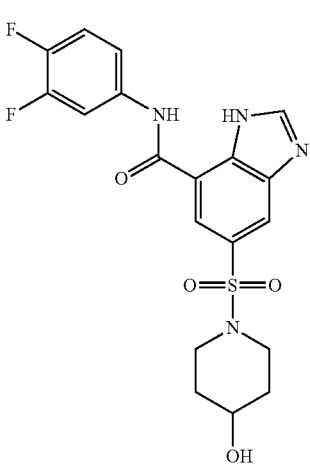 [SMILES: O=C(Nc1ccc(F)c(F)c1)c1cc(S(=O)(=O)N2CCC(O)CC2)cc2nc[nH]c12] | 1502 | | |

TABLE 1-continued

| Structure | Compound ID | ¹H NMR | MS (M + H)⁺ |
|---|---|---|---|
| 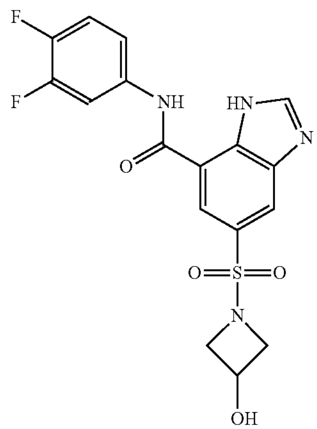 [SMILES: O=C(Nc1ccc(F)c(F)c1)c1cc(S(=O)(=O)N2CC(O)C2)cc2nc[nH]c12] | 1503 | | |
| 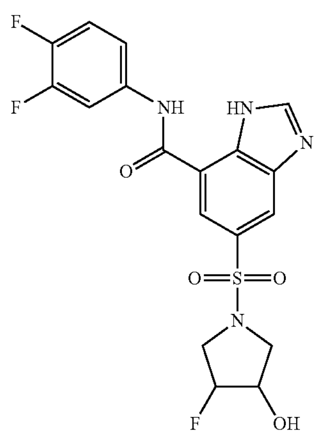 [SMILES: O=C(Nc1ccc(F)c(F)c1)c1cc(S(=O)(=O)N2CC(O)C(F)C2)cc2nc[nH]c12] | 1504 | | |
| 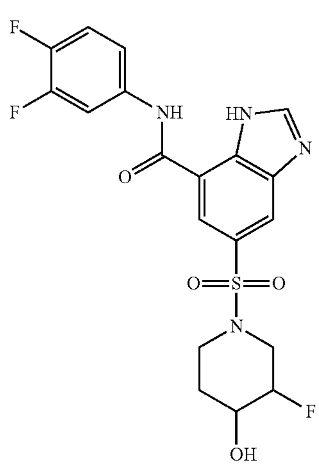 [SMILES: O=C(Nc1ccc(F)c(F)c1)c1cc(S(=O)(=O)N2CCC(O)C(F)C2)cc2nc[nH]c12] | 1505 | | |

TABLE 1-continued

| Structure | Compound ID | ¹H NMR | MS (M + H)⁺ |
|---|---|---|---|
| 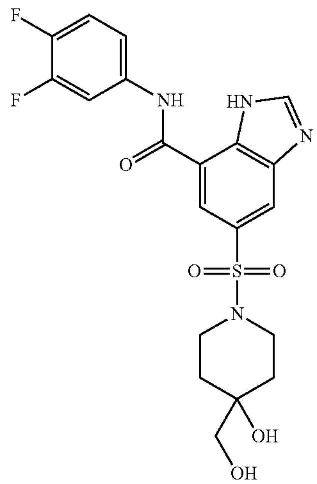 [SMILES: O=C(Nc1ccc(F)c(F)c1)c1cc(S(=O)(=O)N2CCC(O)(CO)CC2)cc2nc[nH]c12] | 1506 | | |
| 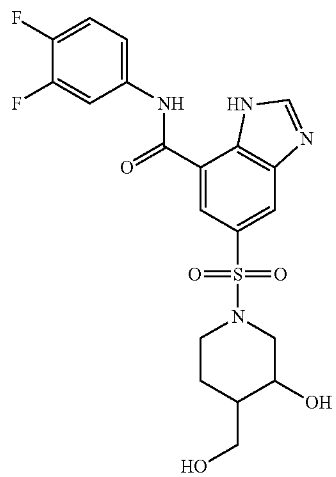 [SMILES: O=C(Nc1ccc(F)c(F)c1)c1cc(S(=O)(=O)N2CCC(CO)C(O)C2)cc2nc[nH]c12] | 1507 | | |
| 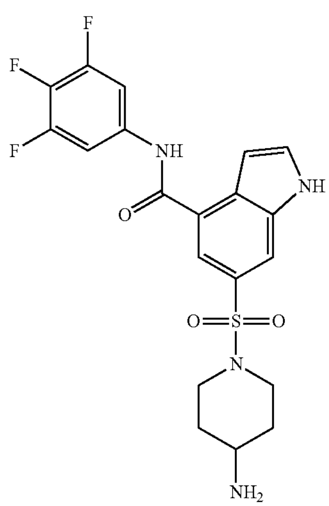 [SMILES: NC1CCN(S(=O)(=O)c2cc(C(=O)Nc3cc(F)c(F)c(F)c3)c3cc[nH]c3c2)CC1] | 1508 | | 453 |

TABLE 1-continued

| Structure | Compound ID | ¹H NMR | MS (M + H)⁺ |
|---|---|---|---|
| (structure) | 1533 | | 498 |
| (structure) | 1534 | 1H NMR (400 MHz MeOD-d4) 8.07 (s, 1H), 8.03 (s, 1H), 7.89 (s, 1H), 7.72-7.47 (m, 2H), 7.28 (t, J = 8.8 HZ, 1H), 7.00 (s, 1H), 3.63-3.57 (m, 5H), 3.33 (s, 3H), 3.18 (s, 2H), 2.81-2.63 (m, 2H) 1.81-1.61 (m, 4H) | 496 |
| (structure) | 1535 | | 480 |

TABLE 1-continued

| Structure | Compound ID | ¹H NMR | MS (M + H)⁺ |
|---|---|---|---|
| 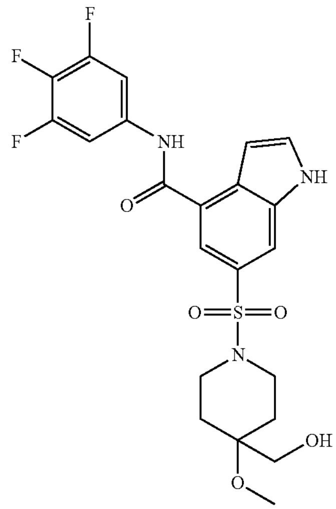 [SMILES: COC1(CO)CCN(S(=O)(=O)c2cc(C(=O)Nc3cc(F)c(F)c(F)c3)c3cc[nH]c3c2)CC1] | 1536 | | 498 |
| 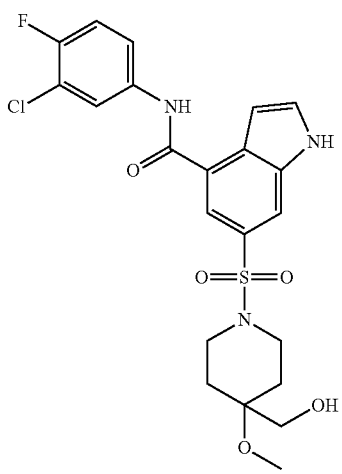 [SMILES: COC1(CO)CCN(S(=O)(=O)c2cc(C(=O)Nc3ccc(F)c(Cl)c3)c3cc[nH]c3c2)CC1] | 1537 | 1H NMR (400 MHz MeOD-d4) 8.07 (s, 1H), 8.03 (s, 1H), 7.89 (s, 1H), 7.72-7.67 (m, 2H), 7.28 (t, J = 8.8 HZ, 1H), 6.99 (s, 1H), 3.63-3.31 (m, 5H), 3.18 (s, 2H), 2.75-2.63 (m, 2H), 1.81-1.57 (m, 4H) | 496 |
| 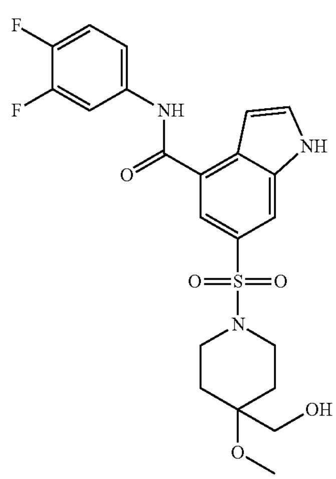 [SMILES: COC1(CO)CCN(S(=O)(=O)c2cc(C(=O)Nc3ccc(F)c(F)c3)c3cc[nH]c3c2)CC1] | 1538 | | 480 |

TABLE 1-continued

| Structure | Compound ID | ¹H NMR | MS (M + H)⁺ |
|---|---|---|---|
| 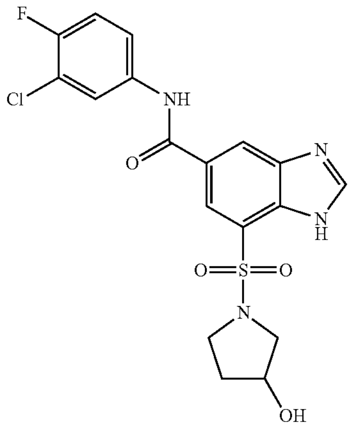 [SMILES: O=C(Nc1ccc(F)c(Cl)c1)c1cc(S(=O)(=O)N2CCC(O)C2)c2[nH]cnc2c1] | 1569 | | |
| 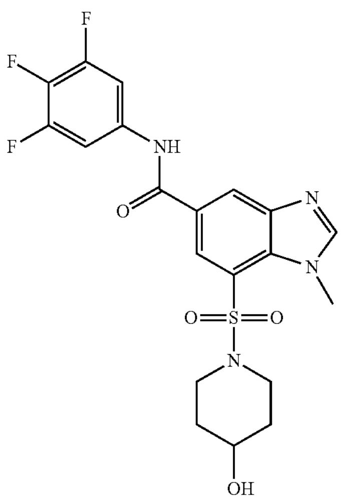 [SMILES: Cn1cnc2cc(C(=O)Nc3cc(F)c(F)c(F)c3)cc(S(=O)(=O)N3CCC(O)CC3)c21] | 1571 | | |
| 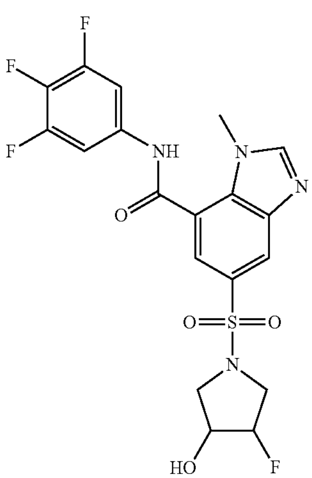 [SMILES: Cn1cnc2cc(S(=O)(=O)N3CC(O)C(F)C3)cc(C(=O)Nc3cc(F)c(F)c(F)c3)c21] | 1572 | | |

TABLE 1-continued

| Structure | Compound ID | ¹H NMR | MS (M + H)⁺ |
|---|---|---|---|
| (structure) | 1573 | | |
| (structure) | 1574 | | |
| (structure) | 1575 | | |

Preparation of the Compounds of the Invention

The compounds of the invention may possess one or more stereocenters, and each stereocenter may exist independently in either the R or S configuration. In one embodiment, compounds described herein are present in optically active or racemic forms. It is to be understood that the compounds described herein encompass racemic, optically-active, regioisomeric and stereoisomeric forms, or combinations thereof that possess the therapeutically useful properties described herein.

Preparation of optically active forms is achieved in any suitable manner, including by way of non-limiting example, by resolution of the racemic form with recrystallization techniques, synthesis from optically-active starting materials, chiral synthesis, or chromatographic separation using a chiral stationary phase. In one embodiment, a mixture of one or more isomer is utilized as the therapeutic compound described herein. In another embodiment, compounds described herein contain one or more chiral centers. These compounds are prepared by any means, including stereoselective synthesis, enantioselective synthesis and/or separation of a mixture of enantiomers and/or diastereomers. Resolution of compounds and isomers thereof is achieved by any means including, by way of non-limiting example, chemical processes, enzymatic processes, fractional crystallization, distillation, and chromatography.

The methods and formulations described herein include the use of N-oxides (if appropriate), crystalline forms (also known as polymorphs), solvates, amorphous phases, and/or pharmaceutically acceptable salts of compounds having the structure of any compound of the invention, as well as metabolites and active metabolites of these compounds having the same type of activity. Solvates include water, ether (e.g., tethrahydrofuran, methyl tert-butyl ether) or alcohol (e.g., ethanol) solvates, acetates and the like. In one embodiment, the compounds described herein exist in solvated forms with pharmaceutically acceptable solvents such as water, and ethanol. In another embodiment, the compounds described herein exist in unsolvated form. In one embodiment, the compounds of the invention may exist as tautomers. All tautomers are included within the scope of the compounds presented herein.

In one embodiment, compounds described herein are prepared as prodrugs. A "prodrug" refers to an agent that is converted into the parent drug in vivo. In one embodiment, upon in vivo administration, a prodrug is chemically converted to the biologically, pharmaceutically or therapeutically active form of the compound. In another embodiment, a pro drug is enzymatically metabolized by one or more steps or processes to the biologically, pharmaceutically or therapeutically active form of the compound.

In one embodiment, sites on, for example, the aromatic ring portion of compounds of the invention are susceptible to various metabolic reactions. Incorporation of appropriate substituents on the aromatic ring structures may reduce, minimize or eliminate this metabolic pathway. In one embodiment, the appropriate substituent to decrease or eliminate the susceptibility of the aromatic ring to metabolic reactions is, by way of example only, a deuterium, a halogen, or an alkyl group.

Compounds described herein also include isotopically-labeled compounds wherein one or more atoms is replaced by an atom having the same atomic number, but an atomic mass or mass number different from the atomic mass or mass number usually found in nature. Examples of isotopes suitable for inclusion in the compounds described herein include and are not limited to $^{2}H$, $^{3}H$, $^{11}C$, $^{13}C$, $^{14}C$, $^{36}Cl$, $^{18}F$, $^{123}I$, $^{125}I$, $^{13}N$, $^{15}N$, $^{15}O$, $^{17}O$, $^{18}O$, $^{32}P$, and $^{35}S$. In one embodiment, isotopically-labeled compounds are useful in drug and/or substrate tissue distribution studies. In another embodiment, substitution with heavier isotopes such as deuterium affords greater metabolic stability (for example, increased in vivo half-life or reduced dosage requirements). In yet another embodiment, substitution with positron emitting isotopes, such as $^{11}C$, $^{18}F$, $^{15}O$ and $^{13}N$, is useful in Positron Emission Topography (PET) studies for examining substrate receptor occupancy. Isotopically-labeled compounds are prepared by any suitable method or by processes using an appropriate isotopically-labeled reagent in place of the non-labeled reagent otherwise employed.

In one embodiment, the compounds described herein are labeled by other means, including, but not limited to, the use of chromophores or fluorescent moieties, bioluminescent labels, or chemiluminescent labels.

The compounds described herein, and other related compounds having different substituents are synthesized using techniques and materials described herein and as described, for example, in Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), Larock's Comprehensive Organic Transformations (VCH Publishers Inc., 1989), March, Advanced Organic Chemistry $4^{th}$ Ed., (Wiley 1992); Carey and Sundberg, Advanced Organic Chemistry 4th Ed., Vols. A and B (Plenum 2000, 2001), and Green and Wuts, Protective Groups in Organic Synthesis 3rd Ed., (Wiley 1999) (all of which are incorporated by reference for such disclosure). General methods for the preparation of compound as described herein are modified by the use of appropriate reagents and conditions, for the introduction of the various moieties found in the formula as provided herein.

Compounds described herein are synthesized using any suitable procedures starting from compounds that are available from commercial sources, or are prepared using procedures described herein.

In one embodiment, reactive functional groups, such as hydroxyl, amino, imino, thio or carboxy groups, are protected in order to avoid their unwanted participation in reactions. Protecting groups are used to block some or all of the reactive moieties and prevent such groups from participating in chemical reactions until the protective group is removed. In another embodiment, each protective group is removable by a different means. Protective groups that are cleaved under totally disparate reaction conditions fulfill the requirement of differential removal.

Protecting groups, plus a detailed description of techniques applicable to the creation of protecting groups and their removal are described in Greene and Wuts, Protective Groups in Organic Synthesis, 3rd Ed., John Wiley & Sons, New York, N.Y., 1999, and Kocienski, Protective Groups, Thieme Verlag, New York, N.Y., 1994, which are incorporated herein by reference for such disclosure.

Assays

HBV Capsid Protein Assembly Testing

The fluorescence quenching in vitro assembly HBV assay was developed according to a method described by Zlotnick and coworkers (Nature Biotechnology 2006, 24:358). The assay is based on the observation that the C-termini of the HBV core protein cluster together during capsid formation. This assay utilizes a mutant C150 HBV capsid protein where all wild-type cysteines are mutated to alanines, but a C-terminal cysteine residue is preserved and is labeled with fluorescent BoDIPY-FL dye. HBV C150Bo protein is highly fluorescent, however the fluorescence is drastically reduced during the capsid assembly process. Thus, the assay measures the ability and potency of test compounds to modulate capsid assembly by monitoring the fluorescence of the labeled capsid C150Bo protein.

In a typical assay, the mutant HBV C150 protein (amino acids 1-150, C49A, C61A, C107A, 150C) is cloned into a T7 RNA-polymerase based expression vector, expressed in E. coli and purified to homogeneity as a dimer. The purified HBV core protein is desalted and labeled with BODIPY-FL Dye.

In a non-limiting embodiment, the assembly assay is conducted in 96-well plate format. The assembly reactions are carried out in 50 mM Hepes buffer, pH 7.5 and 150 mM NaCl.

The compounds are pre-incubated with the HBV CA protein for 15 min, and the assembly reactions are initiated by addition of NaCl. The reaction is allowed to continue for 1 hour at room temperature.

To determine the effect on capsid assembly, each test compound is initially screened at 4 different concentrations: 10 µM, 3 µM, 1 µM and 0.3 µM in duplicates. Primary hits are compounds that show activity in the assembly assay with $EC_{50}$ less than 10 uM and a representative group of these active compounds is shown in Table 2. Identified primary hits are confirmed in follow-up studies as described elsewhere herein. Known modulators of HBV CA assembly, such as HAP-1 and BAY 41-4109, are used as control compounds in these experiments and exhibited $EC_{50}$ values consistent with the literature. $EC_{50}$ values for test compounds are determined via analysis of the dose-response curve.

HBV Antiviral Testing

Compounds active in the HBV assembly assay are tested for their activity and toxicity in cellular assay. In the first anti-viral assay, the ability of compounds to inhibit HBV replication in an HBV-producing hepatoma cell line using the dot-blot method is evaluated.

Briefly, confluent monolayers of HepG2-2.2.15 cells are incubated with complete medium containing various concentrations of a test compound. Three days later, the culture medium is replaced with fresh medium containing the appropriately diluted test compound. Six days following the initial administration of the test compound, the cell culture supernatant is collected, and cell lysis is performed. The samples are applied onto Nylos membranes and DNA is immobilized to the membrane by UV cross-linking. After pre-hybridization, the HBV probe is added and the hybridization is performed overnight. The membranes are exposed to the Kodak films; antiviral activity is calculated from the reduction in HBV DNA levels ($EC_{50}$). The $EC_{50}$ for antiviral activity is calculated from the dose response curves of active compounds. Assay performance over time is monitored by the use of the standard positive control compounds ETV, BAY 41-4109, and HAP-1.

Compound cytotoxicity ($TC_{50}$) is measured in this same HepG2-2.2.15 cell line using a CellTiter Blue-based cytotoxicity assay employed as recommended by manufacturer (Promega). To confirm and expand these results, a second antiviral assay is carried out on active compounds using the stable HBV cell line HepG2.2.15 and measuring anti-HBV potency by real-time PCR and cytotoxicity by CellTiter Blue. In this assay, 24 hours after cell seeding, HepG2-2.2.15 cells are incubated with complete medium containing various concentrations of a test compound with BAY 41-4109 and HAP-1 used as positive controls. After three days, the culture medium is replaced with fresh medium containing the appropriately diluted test compound. The cell culture is collected six days following the initial administration of the test compound, followed by HBV DNA extraction using QIAamp 96 DNA Blood Kit (Qiagen). The extracted HBV DNA is diluted and analyzed by Real-Time PCR. A standard curve is generated by plotting Ct value vs the amount of HBV plasmid standard. Cytotoxicity is determined similarly to the above described method by applying a dye uptake method (CellTiter Blue kit, Promega).

Prevention of HBV Pre-Genomic RNA (pgRNA) Incorporation

The anti-viral activity of the compounds of the invention is assessed based on their ability to suppress both extracellular and intracellular HBV DNA production in two different cell culture models of HBV replication. To assess if these effects are due to disruption of intracellular capsid assembly, a particle-gel assay that allows quantitation of intracellular viral capsids, as well as encapsidated pre-genomic RNA and DNA, is performed. The assay relies on agarose gel separation of viral capsid from free capsid/core subunits and viral pg-RNA and DNA.

Methods of Treatment

The invention includes a method of treatment of an HBV infection in an individual in need thereof, comprising administering to the individual a therapeutically effective amount of a compound of the invention.

The invention also includes a method of reducing viral load associated with an HBV infection in an individual in need thereof, comprising administering to the individual a therapeutically effective amount of a compound of the invention.

The invention further includes a method of reducing reoccurrence of an HBV infection in an individual in need thereof, comprising administering to the individual a therapeutically effective amount of a compound of the invention.

The invention also includes a method of reducing an adverse physiological impact of an HBV infection in an individual in need thereof, comprising administering to the individual a therapeutically effective amount of a compound of the invention.

The invention includes a method of reducing, slowing, or inhibiting an HBV infection in an individual in need thereof, comprising administering to the individual a therapeutically effective amount of a compound of the invention.

The invention also includes a method of inducing remission of hepatic injury from an HBV infection in an individual in need thereof, comprising administering to the individual a therapeutically effective amount of a compound of the invention.

The invention further includes a method of reducing the physiological impact of long-term antiviral therapy for HBV infection in an individual in need thereof, comprising administering to the individual a therapeutically effective amount of a compound of the invention.

The invention also includes a method of eradicating an HBV infection in an individual in need thereof, comprising administering to the individual a therapeutically effective amount of a compound of the invention.

The invention further includes a method of prophylactically treating an HBV infection in an individual in need thereof, wherein the individual is afflicted with a latent HBV infection, comprising administering to the individual a therapeutically effective amount of a compound of the invention.

In one embodiment, the methods described herein further comprise administering at least one therapeutic agent selected from the group consisting of nucleotide/nucleoside analogs, entry inhibitors, fusion inhibitors, interferon agents, and any combination of those or other antiviral mechanisms. In another embodiment, the compound of the invention and the at least one additional therapeutic agent are co-formulated. In yet another embodiment, the compound of the invention and the at least one additional therapeutic agent are co-administered.

In one embodiment, the individual is refractory to other therapeutic classes of HBV drugs (e.g, HBV polymerase inhibitors, interferons, viral entry inhibitors, viral maturation inhibitors, distinct capsid assembly modulators, antiviral compounds of distinct or unknown mechanism, and the like, or combinations thereof). In another embodiment, the method of the invention reduces viral load in an individual suffering from an HBV infection to a greater extent compared to the extent that other therapeutic classes of HBV drugs reduce viral load in the individual.

In one embodiment, the method of the invention reduces viral load in an individual suffering from an HBV infection, thus allowing lower doses or varying regimens of combination therapies to be used.

In one embodiment, the method of the invention causes a lower incidence of viral mutation and/or viral resistance compared to other classes of HBV drugs, thereby allowing for long term therapy and minimizing the need for changes in treatment regimens.

In one embodiment, the method of the invention increases the seroconversion rate beyond that of current treatment regimens.

In one embodiment, the method of the invention increases and/or normalizes and/or restores normal health, elicits full recovery of normal health, restores life expectancy, and/or resolves the viral infection in the individual in need thereof.

In one embodiment, the method of the invention eradicates HBV from an individual infected with HBV, thereby obviating the need for long term and/or life-long treatment, or shortening the duration of treatment, and/or allowing for reduction in dosing of other antiviral agents.

Accordingly, in one embodiment, provided herein is a method of treating an HBV infection in an individual in need thereof, comprising administering to the individual a therapeutically effective amount of a compound of Formula I, or a pharmaceutically acceptable salt thereof.

In another embodiment, provided herein is a method of treating an HBV infection in an individual in need thereof, comprising administering to the individual a therapeutically effective amount of a compound of Formula II, or a pharmaceutically acceptable salt thereof.

In another embodiment, provided herein is a method of treating an HBV infection in an individual in need thereof, comprising administering to the individual a therapeutically effective amount of a compound of Formula III, or a pharmaceutically acceptable salt thereof.

In another embodiment, provided herein is a method of treating an HBV infection in an individual in need thereof, comprising administering to the individual a therapeutically effective amount of a compound of Formula IV, or a pharmaceutically acceptable salt thereof.

In another embodiment, provided herein is a method of treating an HBV infection in an individual in need thereof, comprising administering to the individual a therapeutically effective amount of a compound of Formula V, or a pharmaceutically acceptable salt thereof.

In another embodiment, provided herein is a method of treating an HBV infection in an individual in need thereof, comprising administering to the individual a therapeutically effective amount of a compound of Formula VI, or a pharmaceutically acceptable salt thereof.

In another embodiment, provided herein is a method of treating an HBV infection in an individual in need thereof, comprising administering to the individual a therapeutically effective amount of a compound of Formula VII, or a pharmaceutically acceptable salt thereof.

In another embodiment, provided herein is a method of treating an HBV infection in an individual in need thereof, comprising administering to the individual a therapeutically effective amount of a compound of Formula VIII, or a pharmaceutically acceptable salt thereof.

In another embodiment, provided herein is a method of treating an HBV infection in an individual in need thereof, comprising administering to the individual a therapeutically effective amount of a compound of Formula IX, or a pharmaceutically acceptable salt thereof.

In another embodiment, provided herein is a method of treating an HBV infection in an individual in need thereof, comprising administering to the individual a therapeutically effective amount of a compound of Formula X, or a pharmaceutically acceptable salt thereof.

In another embodiment, provided herein is a method of treating an HBV infection in an individual in need thereof, comprising administering to the individual a therapeutically effective amount of a compound of Formula XI, or a pharmaceutically acceptable salt thereof.

In another embodiment, provided herein is a method of treating an HBV infection in an individual in need thereof, comprising administering to the individual a therapeutically effective amount of a compound of Formula XII, or a pharmaceutically acceptable salt thereof.

Accordingly, in one embodiment, provided herein is a method of treating an HBV infection in an individual in need thereof, comprising administering to the individual a therapeutically effective amount of a compound of Table 1, or a pharmaceutically acceptable salt thereof.

Combination Therapies

The compounds of the present invention are intended to be useful in combination with one or more additional compounds useful for treating HBV infection. These additional compounds may comprise compounds of the present invention or compounds known to treat, prevent, or reduce the symptoms or effects of HBV infection. Such compounds include but are not limited to HBV polymerase inhibitors, interferons, pegylated interferons, viral entry inhibitors, viral maturation inhibitors, literature-described capsid assembly modulators, and other agents with distinct or unknown mechanisms that affect the HBV life cycle and/or affect the consequences of HBV infection.

In non-limiting examples, the compounds of the invention may be used in combination with one or more drugs (or a salt, solvate or prodrug thereof) selected from the group consisting of:

HBV reverse transcriptase inhibitors, and DNA and RNA polymerase inhibitors, including but are not limited to: lamivudine (3TC, Zeffix, Heptovir, Epivir, and Epivir-HBV), entecavir (Baraclude, Entavir), adefovir dipivoxil (Hepsara, Preveon, bis-POM PMEA), tenofovir disoproxil fumarate (Viread, TDF or PMPA);

Interferons and pegylated interferons, including but not limited to interferon alpha (IFN-α), interferon lambda (IFN-λ), and interferon gamma (IFN-γ);

viral entry inhibitors;

viral maturation inhibitors;

literature-described capsid assembly modulators, such as but not limited to BAY 41-4109;

compounds of distinct or unknown mechanism, such as but not limited to AT-61 ((E)-N-(1-chloro-3-oxo-1-phenyl-3-(piperidin-1-yl)prop-1-en-2-yl)benzamide), AT-130 ((E)-N-(1-bromo-1-(2-methoxyphenyl)-3-oxo-3-(piperidin-1-yl)prop-1-en-2-yl)-4-nitrobenzamide), and similar analogs.

In one embodiment, the additional therapeutic agent is a pegylated interferon alpha drug, including, but not limited to, PEGASYS®.

In another embodiment, the additional therapeutic agent selected from immune modulator or immune stimulator therapies, which includes biological agents belonging to the interferon class, such as interferon alpha 2a or 2b or modified interferons such as pegylated interferon, alpha 2a, alpha 2b, lamda; or TLR modulators such as TLR-7 agonists or TLR-9 agonists, or antiviral agents that block viral entry or maturation or target the HBV polymerase such as nucleoside or nucleotide or non-nucleos(t)ide polymerase inhibitors, and agents of distinct or unknown mechanism including agents that disrupt the function of other essential viral protein(s) or host proteins required for HBV replication or persistence.

In an embodiment of the combination therapy, the reverse transcriptase inhibitor and/or DNA and/or RNA polymerase inhibitor Zidovudine, Didanosine, Zalcitabine, ddA, Stavudine, Lamivudine, Abacavir, Emtricitabine, Entecavir, Apricitabine, Atevirapine, ribavirin, acyclovir, famciclovir, valacyclovir, ganciclovir, valganciclovir, Tenofovir, Adefovir, PMPA, cidofovir, Efavirenz, Nevirapine, Delavirdine, or Etravirine.

In another embodiment of the combination therapy, the TLR-7 agonist is selected from the group consisting of SM360320 (9-benzyl-8-hydroxy-2-(2-methoxy-ethoxy)adenine) and AZD 8848 (methyl[3-({[3-(6-amino-2-butoxy-8-oxo-7,8-dihydro-9H-purin-9-yl)propyl][3-(4-morpholinyl)propyl]amino}methyl)phenyl]acetate).

A synergistic effect may be calculated, for example, using suitable methods such as, for example, the Sigmoid-$E_{max}$ equation (Holford & Scheiner, 19981, Clin. Pharmacokinet. 6: 429-453), the equation of Loewe additivity (Loewe & Muischnek, 1926, Arch. Exp. Pathol Pharmacol. 114: 313-326) and the median-effect equation (Chou & Talalay, 1984, Adv. Enzyme Regul. 22: 27-55). Each equation referred to above may be applied to experimental data to generate a corresponding graph to aid in assessing the effects of the drug combination. The corresponding graphs associated with the equations referred to above are the concentration-effect curve, isobologram curve and combination index curve, respectively.

Administration/Dosage/Formulations

The regimen of administration may affect what constitutes an effective amount. The therapeutic formulations may be administered to the patient either prior to or after the onset of a HBV infection. Further, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Administration of the compositions of the present invention to a patient, preferably a mammal, more preferably a human, may be carried out using known procedures, at dosages and for periods of time effective to treat HBV infection in the patient. An effective amount of the therapeutic compound necessary to achieve a therapeutic effect may vary according to factors such as the state of the disease or disorder in the patient; the age, sex, and weight of the patient; and the ability of the therapeutic compound to treat HBV infection in the patient. Dosage regimens may be adjusted to provide the optimum therapeutic response. For example, several divided doses may be administered daily or the dose may be proportionally reduced as indicated by the exigencies of the therapeutic situation. A non-limiting example of an effective dose range for a therapeutic compound of the invention is from about 1 and 5,000 mg/kg of body weight/per day. One of ordinary skill in the art would be able to study the relevant factors and make the determination regarding the effective amount of the therapeutic compound without undue experimentation.

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

In particular, the selected dosage level will depend upon a variety of factors including the activity of the particular compound employed, the time of administration, the rate of excretion of the compound, the duration of the treatment, other drugs, compounds or materials used in combination with the compound, the age, sex, weight, condition, general health and prior medical history of the patient being treated, and like factors well, known in the medical arts.

A medical doctor, e.g., physician or veterinarian, having ordinary skill in the art may readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In particular embodiments, it is especially advantageous to formulate the compound in dosage unit form for ease of administration and uniformity of dosage. Dosage unit form as used herein refers to physically discrete units suited as unitary dosages for the patients to be treated; each unit containing a predetermined quantity of therapeutic compound calculated to produce the desired therapeutic effect in association with the required pharmaceutical vehicle. The dosage unit forms of the invention are dictated by and directly dependent on (a) the unique characteristics of the therapeutic compound and the particular therapeutic effect to be achieved, and (b) the limitations inherent in the art of compounding/formulating such a therapeutic compound for the treatment of HBV infection in a patient.

In one embodiment, the compositions of the invention are formulated using one or more pharmaceutically acceptable excipients or carriers. In one embodiment, the pharmaceutical compositions of the invention comprise a therapeutically effective amount of a compound of the invention and a pharmaceutically acceptable carrier.

The carrier may be a solvent or dispersion medium containing, for example, water, ethanol, polyol (for example, glycerol, propylene glycol, and liquid polyethylene glycol, and the like), suitable mixtures thereof, and vegetable oils. The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, thimerosal, and the like. In many cases, it will be preferable to include isotonic agents, for example, sugars, sodium chloride, or polyalcohols such as mannitol and sorbitol, in the composition. Prolonged absorption of the injectable compositions may be brought about by including in the composition an agent which delays absorption, for example, aluminum monostearate or gelatin. In one embodiment, the pharmaceutically acceptable carrier is not DMSO alone.

In one embodiment, the compositions of the invention are administered to the patient in dosages that range from one to five times per day or more. In another embodiment, the compositions of the invention are administered to the patient in range of dosages that include, but are not limited to, once every day, every two, days, every three days to once a week, and once every two weeks. It will be readily apparent to one skilled in the art that the frequency of administration of the various combination compositions of the invention will vary from individual to individual depending on many factors including, but not limited to, age, disease or disorder to be treated, gender, overall health, and other factors. Thus, the invention should not be construed to be limited to any particular dosage regime and the precise dosage and composition to be administered to any patient will be determined by the attending physical taking all other factors about the patient into account.

Compounds of the invention for administration may be in the range of from about 1 μg to about 10,000 mg, about 20 μg to about 9,500 mg, about 40 μg to about 9,000 mg, about 75 μg to about 8,500 mg, about 150 μg to about 7,500 mg, about 200 μg to about 7,000 mg, about 3050 μg to about 6,000 mg, about 500 μg to about 5,000 mg, about 750 μg to about 4,000 mg, about 1 mg to about 3,000 mg, about 10 mg to about 2,500 mg, about 20 mg to about 2,000 mg, about 25 mg to about 1,500 mg, about 30 mg to about 1,000 mg, about 40 mg to about 900 mg, about 50 mg to about 800 mg, about 60 mg to about 750 mg, about 70 mg to about 600 mg, about 80 mg to about 500 mg, and any and all whole or partial increments therebetween.

In some embodiments, the dose of a compound of the invention is from about 1 mg and about 2,500 mg. In some embodiments, a dose of a compound of the invention used in compositions described herein is less than about 10,000 mg, or less than about 8,000 mg, or less than about 6,000 mg, or less than about 5,000 mg, or less than about 3,000 mg, or less than about 2,000 mg, or less than about 1,000 mg, or less than about 500 mg, or less than about 200 mg, or less than about 50 mg. Similarly, in some embodiments, a dose of a second compound (i.e., a drug used for treating Parkinson's Disease) as described herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments thereof.

In one embodiment, the present invention is directed to a packaged pharmaceutical composition comprising a container holding a therapeutically effective amount of a compound of the invention, alone or in combination with a second pharmaceutical agent; and instructions for using the compound to treat, prevent, or reduce one or more symptoms of HBV infection in a patient.

Formulations may be employed in admixtures with conventional excipients, i.e., pharmaceutically acceptable organic or inorganic carrier substances suitable for oral, parenteral, nasal, intravenous, subcutaneous, enteral, or any other suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They may also be combined where desired with other active agents, e.g., other analgesic agents.

Routes of administration of any of the compositions of the invention include oral, nasal, rectal, intravaginal, parenteral, buccal, sublingual or topical. The compounds for use in the invention may be formulated for administration by any suitable route, such as for oral or parenteral, for example, transdermal, transmucosal (e.g., sublingual, lingual, (trans)buccal, (trans)urethral, vaginal (e.g., trans- and perivaginally), (intra) nasal and (trans)rectal), intravesical, intrapulmonary, intraduodenal, intragastrical, intrathecal, subcutaneous, intramuscular, intradermal, intra-arterial, intravenous, intrabronchial, inhalation, and topical administration.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

The following examples further illustrate aspects of the present invention. However, they are in no way a limitation of the teachings or disclosure of the present invention as set forth herein.

EXAMPLES

The representative synthesis procedures provided below can be used to prepare the compounds of Formula I, e.g., the compounds of Table I. These examples are provided for the purpose of illustration only, and the invention is not limited to these examples, but rather encompasses all variations that are evident as a result of the teachings provided herein.

Unless otherwise noted, all starting materials and resins were obtained from commercial suppliers and used without purification.

1. Preparation of Amine 1 and Amine 2

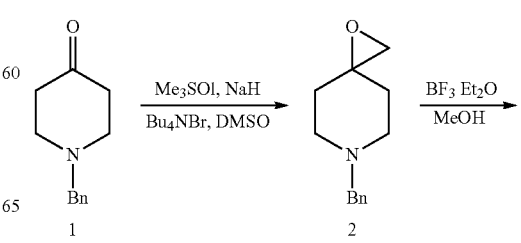

-continued

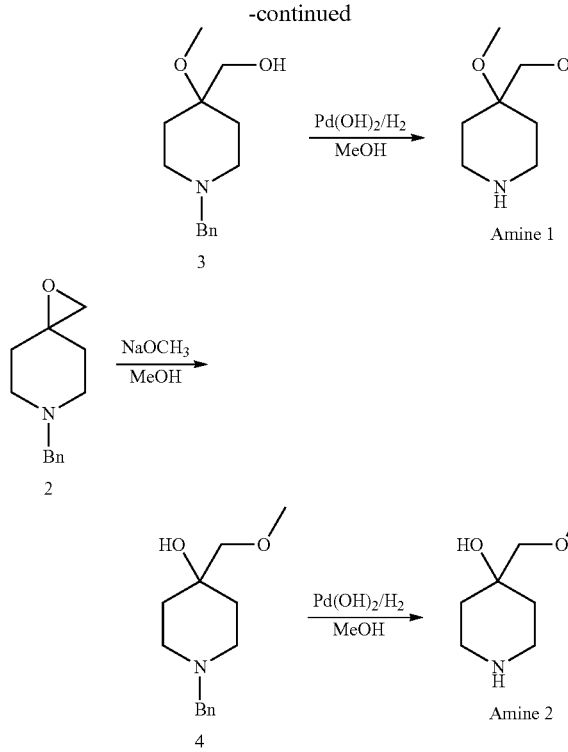

1.1 Preparation of Compound 2

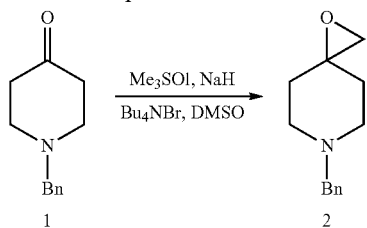

To a solution of Me$_3$SOI (17.5 g, 0.079 mol) in DMSO (80 mL) was added NaH (3.4 g, 0.085 mol) at 0° C. The resulting mixture was stirred at room temperature for 1 hour, then Bu$_4$NBr (1.61 g, 0.005 mol) was added. A solution of Compound 1 (10.0 g, 0.053 mol) in DMSO (40 mL) was added dropwise slowly into the mixture and stirred at room temperature for 2 hour. The mixture was poured into ice water and extracted with EA. The combined organic phases were washed with brine, dried over Na$_2$SO$_4$, and concentrated in vacuum to give the desired product (9.8 g, 91.08%).

1.2 Preparation of Compound 3

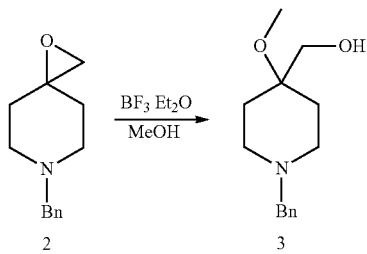

To a solution of Compound 2 (3.0 g, 14.78 mmol) in MeOH (60 mL) was added BF$_3$Et$_2$O (2.52 g, 17.73 mmol) at room temperature. The mixture stirred at room temperature for 12 hours. The reaction was quenched by NaHCO$_3$ solution. The mixture was extracted with EtOAc. The organic layer was concentrated to give the desired Compound 3, and used directly in the next step without further purification (3.2 g, 98%).

1.3 Preparation of Amine 1

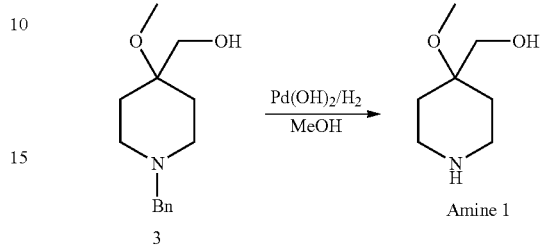

To a solution of Compound 3 (2.3 g, 9.78 mmol) in MeOH was added Pd(OH)$_2$/C (1 g), and the resulting mixture was stirred under H$_2$ balloon atmosphere for 12 hours at 25° C. The mixture was filtered and the filtrate was concentrated to give the desired product as colorless oil (1.3 g, 92%).

1.4 Preparation of Compound 4

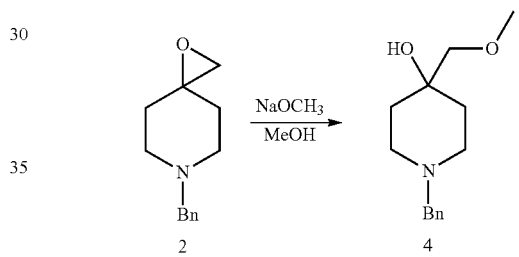

To a solution of Compound 2 (3.0 g, 14.78 mmol) in MeOH (30 mL) was added CH$_3$ONa (2.4 g, 45 mmol) at 0° C. The mixture was stirred at 25° C. for 12 hours. The reaction was quenched with NH$_4$Cl (100 mL) solution, and the mixture was extracted with EtOAc (100 mL). The organic layer was concentrated to give the desired product, and used directly in the next step without further purification (3.2 g, 98%).

1.5 Preparation of Amine 2

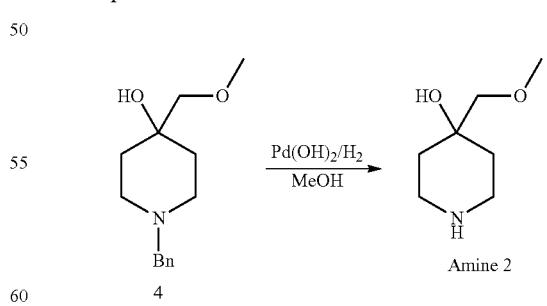

To a solution of Compound 4 (2.3 g, 9.78 mmol) in MeOH was added Pd(OH)$_2$/C (1 g), and the resulting mixture was stirred under H$_2$ balloon atmosphere for 12 hours at 25° C. The mixture was filtered and the filtrate was concentrated to give the desired product as colorless oil (1.3 g, 92%).

2. Preparation of Compound 949

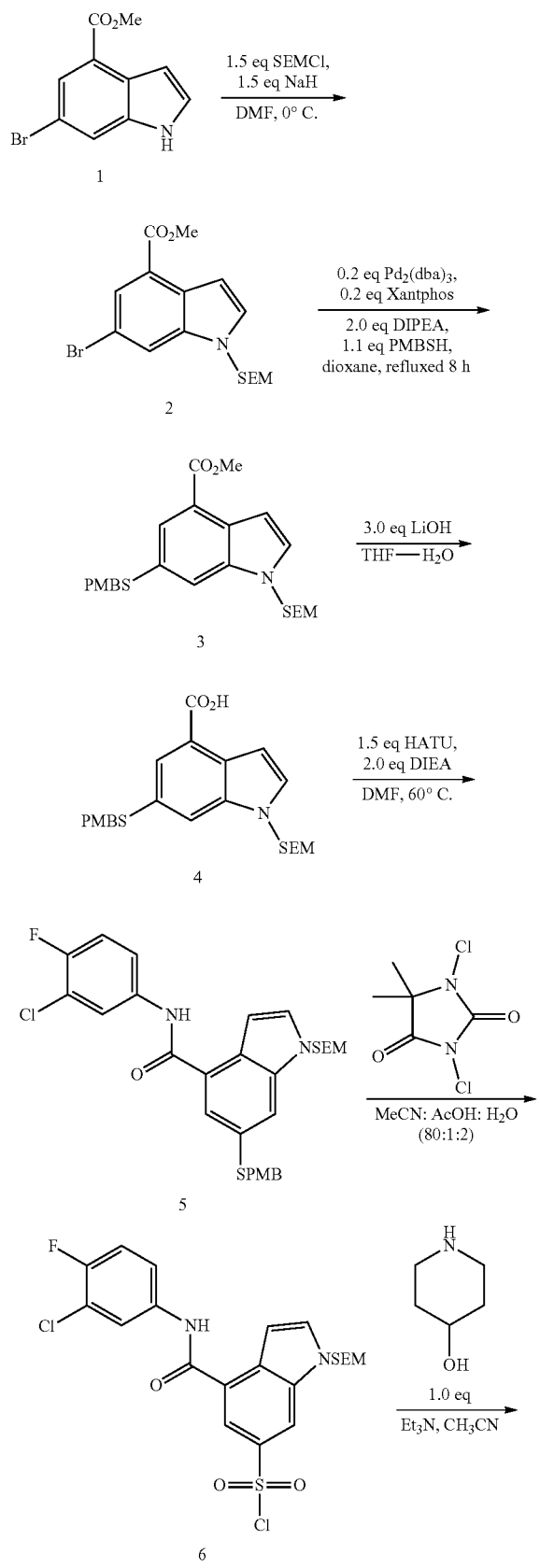

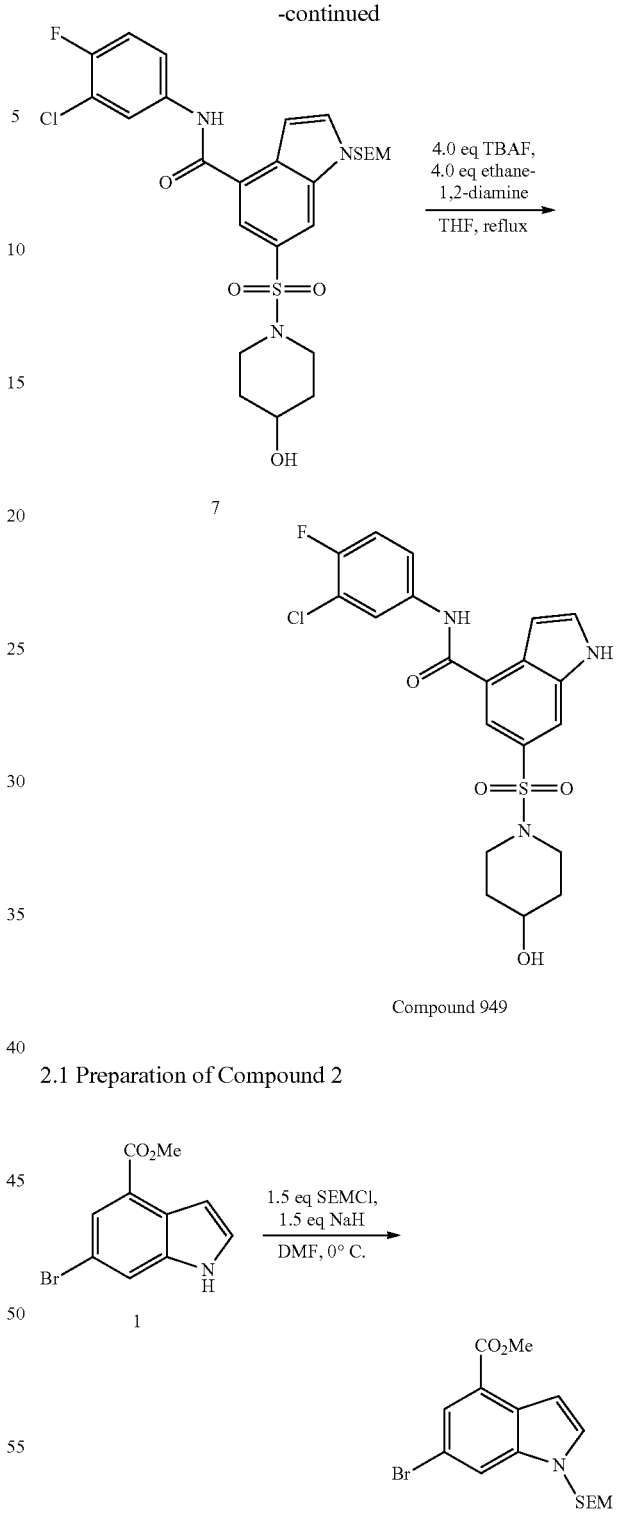

Compound 949

2.1 Preparation of Compound 2

To a solution of Compound 1 (2.5 g, 10 mmol) and in DMF (30 mL) was added NaH (600 mg, 15 mmol) at 0° C., the mixture was stirred at 0° C. for 30 min. Then SEMCl (2.49 g, 15 mmol) was added dropwised at 0° C. and stirred at room temperature for 2 hours. The mixture was diluted with EA (100 mL) and water (50 mL). The organic layer was washed with saturated $NH_4Cl$ (100 mL*3), dried over $Na_2SO_4$, and concentrated in vacuo to give Compound 2 as yellow solid (3.7 g, 98%). LCMS: 384/386 [M+1].

2.2 Preparation of Compound 3

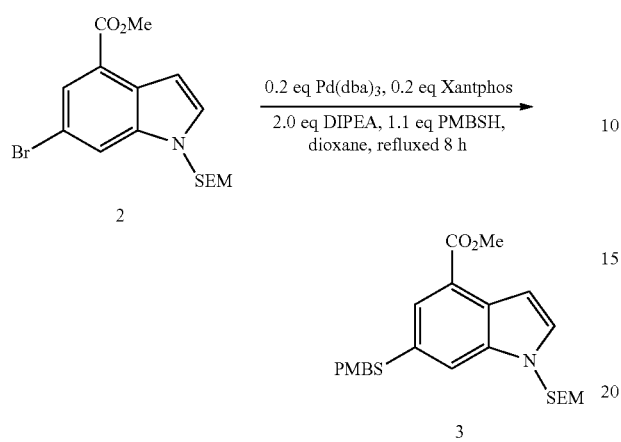

A mixture of Compound 2 (1.92 g, 5 mmol), (4-methoxyphenyl)methanethiol (0.69 g, 5.5 mmol), Pd$_2$(dba)$_3$ (0.23 g, 0.25 mol), Xantphos (0.29 g, 0.5 mmol) and DIPEA (1.29 g, 10 mmol) in dioxane (50 mL) was heated to reflux overnight under N$_2$ atmosphere. The mixture was filtered and the filtrate was concentrated in vacuo. The residue was purified by silica gel chromatography (PE:EA=10:1) to give Compound 3 as yellow solid (2.0 g, 88%). LCMS: 458 [M+1].

2.3 Preparation of Compound 4

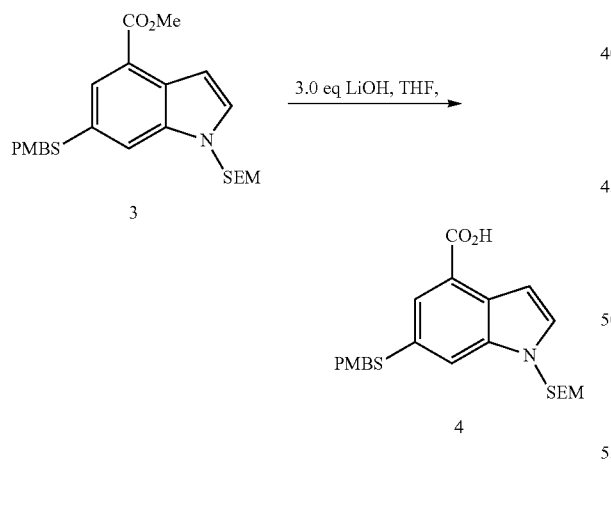

To a stirred solution of Compound 3 (2.2 g, 5 mmol) in THF (20 mL) was added aqueous LiOH (5 mL, 3 M) solution. The mixture was heated to reflux for 2 hours. After cooled to room temperature, the mixture was adjusted pH to 4 with 2 M HCl. The mixture was extracted with EA (100 mL*2). The organic layers was dried over Na$_2$SO$_4$ and concentrated to give desired Compound 4 as yellow solid (2.1 g, 99%). LCMS: 444 [M+1].

2.4 Preparation of Compound 5

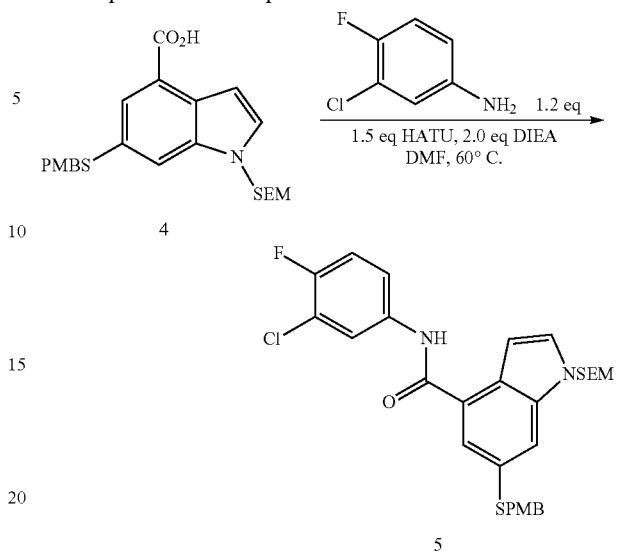

To a solution of Compound 4 (2.2 g, 5 mmol) and 3-chloro-4-fluoroaniline (870 mg, 6 mmol) in DMF (30 mL) was added HATU (2.8 g, 7.5 mmol) and DIEA (967 mg, 7.5 mmol) at room temperature, then the mixture was stirred at 60° C. for 12 h. The mixture was diluted with EA (100 mL). The organic layer was washed by saturated NH$_4$Cl (100 mL*3), dried over Na$_2$SO$_4$, and concentrated in vacuo. The residue was purified by chromatography to give Compound 5 as yellow solid (2.0 g, 70%). LCMS: 571 [M+1].

2.5 Preparation of Compound 6

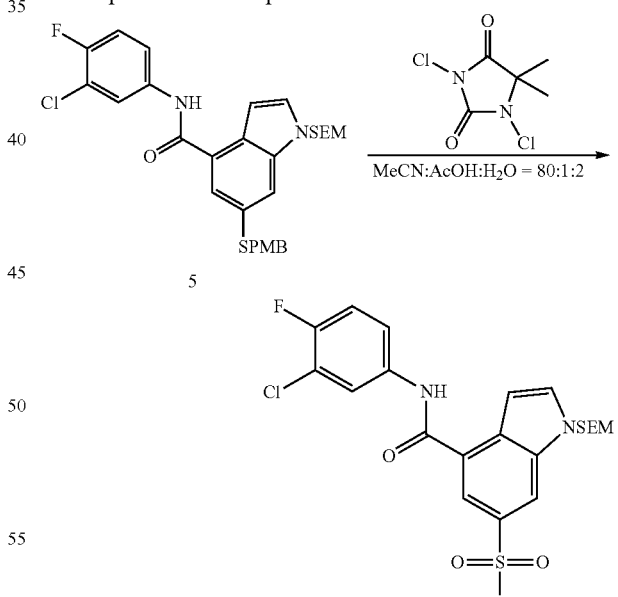

To a suspension of Compound 5 (470 mg, 1 mmol) in MeCN/AcOH/H$_2$O (80/1/2, 5 mL) at −15° C. was added 1,3-dichloro-5,5-dimethylimidazolidine-2,4-dione (290 mg, 1.5 mmol), the mixture was stirred at −15° C. for 8 hours. The residue was used in the next step directly. LCMS: 517/519 [M+1].

2.6 Preparation of Compound 7

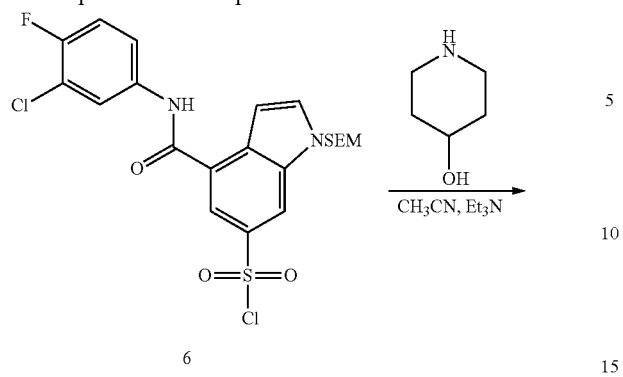

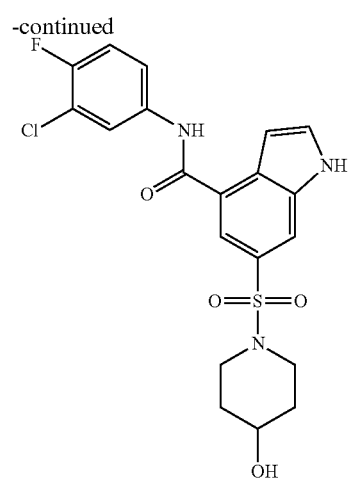

Compound 949

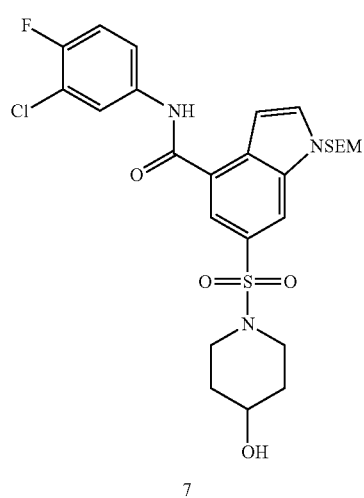

To a mixture of Compound 6 (1 mmol, from the last step) was added piperidin-4-ol (202 mg, 2 mmol) and TEA (400 mg, 4 mmol), the mixture was stirred at room temperature for 1 hour. The solvent was removed and the residue was dissolved in EA (50 mL), the organic layer was washed with saturated NH$_4$Cl (50 mL*2), then dried over Na$_2$SO$_4$ and concentrated to give crude Compound 7 which was used for the next step without further purification. LCMS: 582 [M+1].

2.7 Preparation of Compound 949

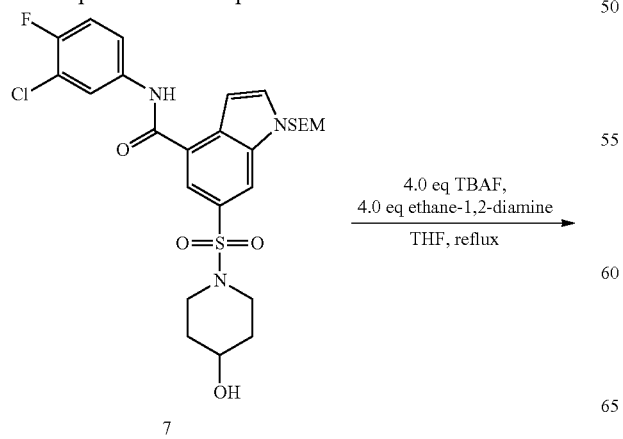

To a solution of Compound 7 (1 mmol, from the last step) in THF (10 mL) was added TBAF (1050 mg, 4 mmol) and ethane-1,2-diamine (240 mg, 4 mmol), the mixture was stirred at 70° C. for 30 hours. The solvent was removed and the residue was purified by pre-HPLC (FA) to give desired Compound 949 (95 mg, yield 21.1% for the three steps) as white solid. $^1$H NMR (400 MHz, MeOD-d4) 8.11 (s, 1H), 8.09-8.05 (m, 1H), 7.92 (s, 1H), 7.76-7.63 (m, 2H), 7.33 (t, J=8.8 Hz, 1H), 7.04 (s, 1H), 3.71-3.62 (m, 1H), 3.51-3.41 (m, 2H), 2.91-2.73 (m, 2H), 2.01-1.91 (m, 2H), 1.67-1.57 (m, 2H). LCMS: 452 [M+1].

3. Preparation of Compound 1472

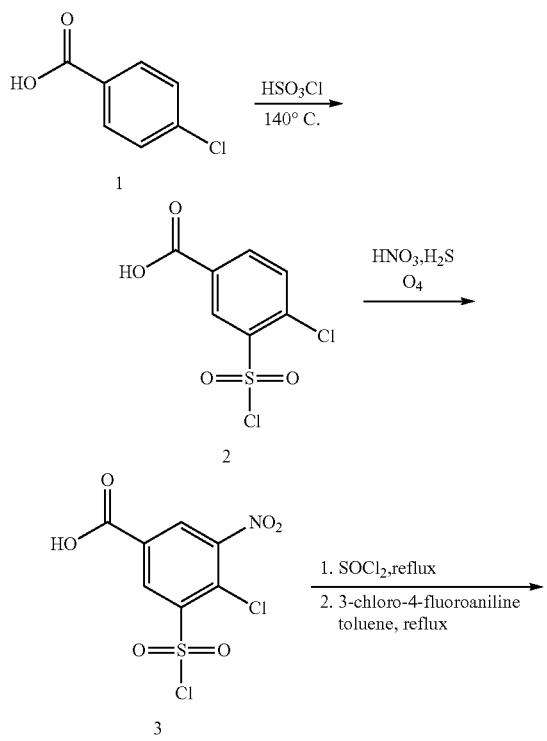

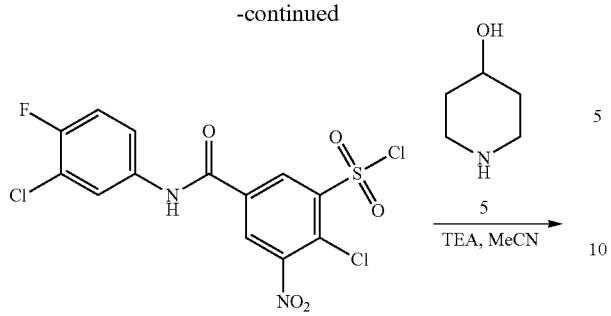
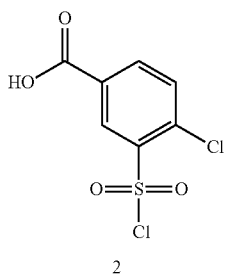
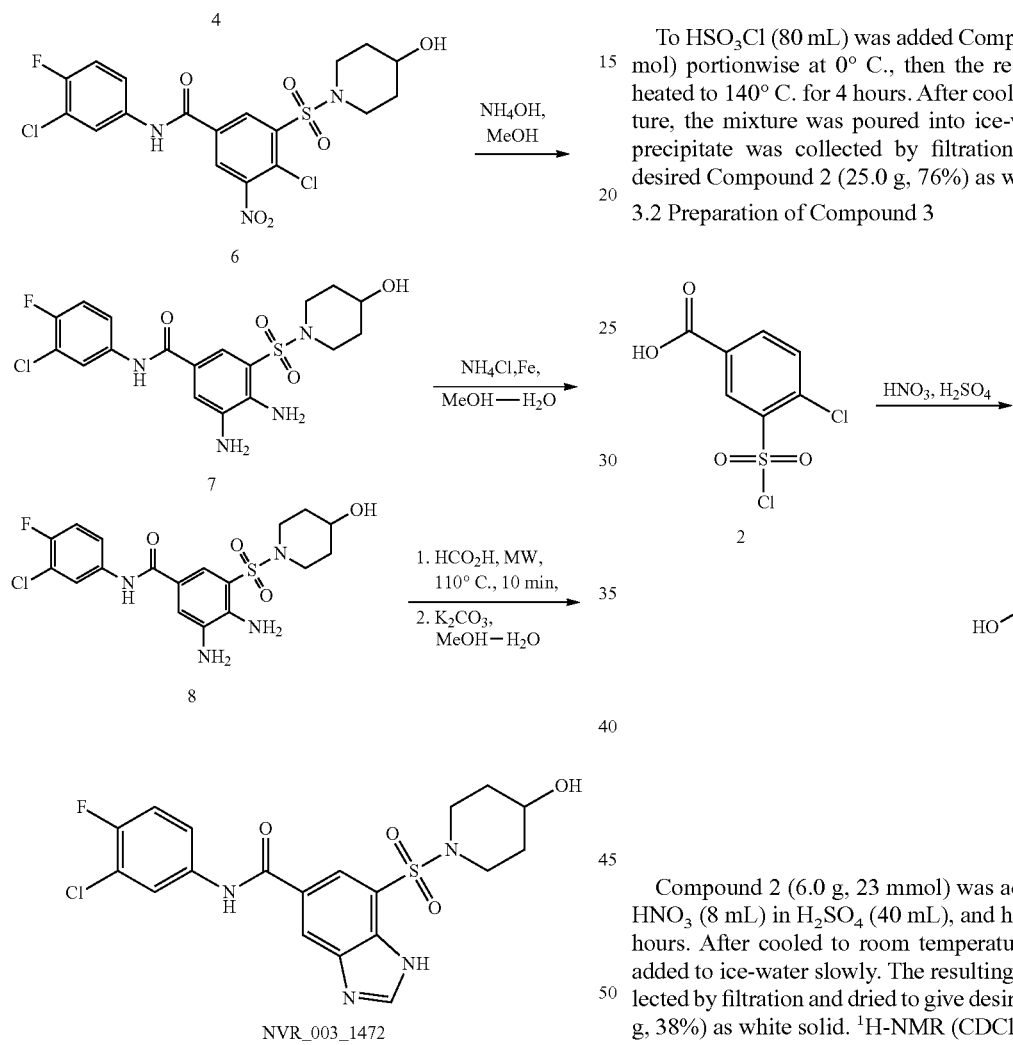

To HSO₃Cl (80 mL) was added Compound 1 (20.0 g, 0.13 mol) portionwise at 0° C., then the resulting mixture was heated to 140° C. for 4 hours. After cooled to room temperature, the mixture was poured into ice-water. The resulting precipitate was collected by filtration and dried to give desired Compound 2 (25.0 g, 76%) as white solid.

3.2 Preparation of Compound 3

Compound 2 (6.0 g, 23 mmol) was added to a mixture of $HNO_3$ (8 mL) in $H_2SO_4$ (40 mL), and heated to 90° C. for 4 hours. After cooled to room temperature, the mixture was added to ice-water slowly. The resulting precipitate was collected by filtration and dried to give desired Compound 3 (2.6 g, 38%) as white solid. ¹H-NMR (CDCl₃, 400 MHz): δ ppm 9.05 (d, J=2.0 Hz, 1H), 8.76 (d, J=2.0 Hz, 1H).

3.3 Preparation of Compound 4

3.1 Preparation of Compound 2

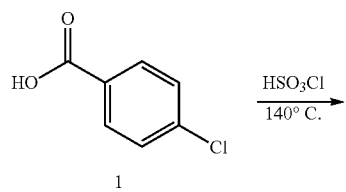
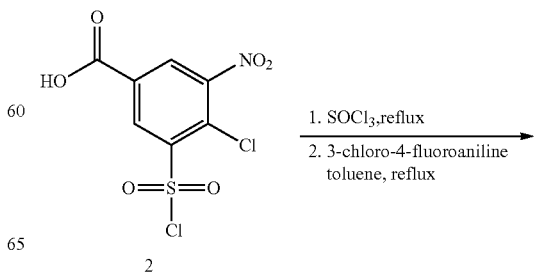

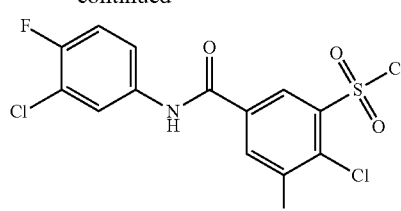

4

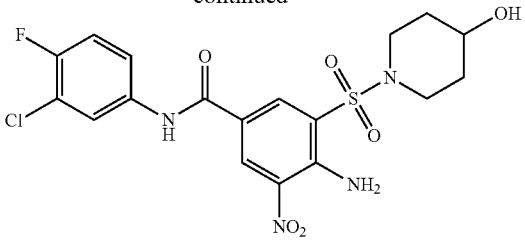

7

A mixture of Compound 3 (0.6 g, 2 mmol) and SOCl₂ (10 mL) was heated to 90° C. for 4 hours. The mixture was concentrated in vacuo. The residue was dissolved with toluene (10 mL) and heated to 90° C. 3-Chloro-4-fluoroaniline (290 mg, 2 mmol) was added and the mixture was continued to heat to reflux for 4 hours. The mixture was concentrated to give desired Compound 4 (0.8 g, crude) as yellow solid, which was used for the next step without further purification.

3.4 Preparation of Compound 6

To a solution of Compound 6 (0.5 g, crude) in MeOH (10 mL) was added ammonia (2 mL, 28%), and the mixture was heated to 70° C. for 4 hours. The mixture was concentrated in vacuo to give desired Compound 7 (0.5 g, crude) as yellow solid, which was used for the next step without purification.

3.6 Preparation of Compound 8

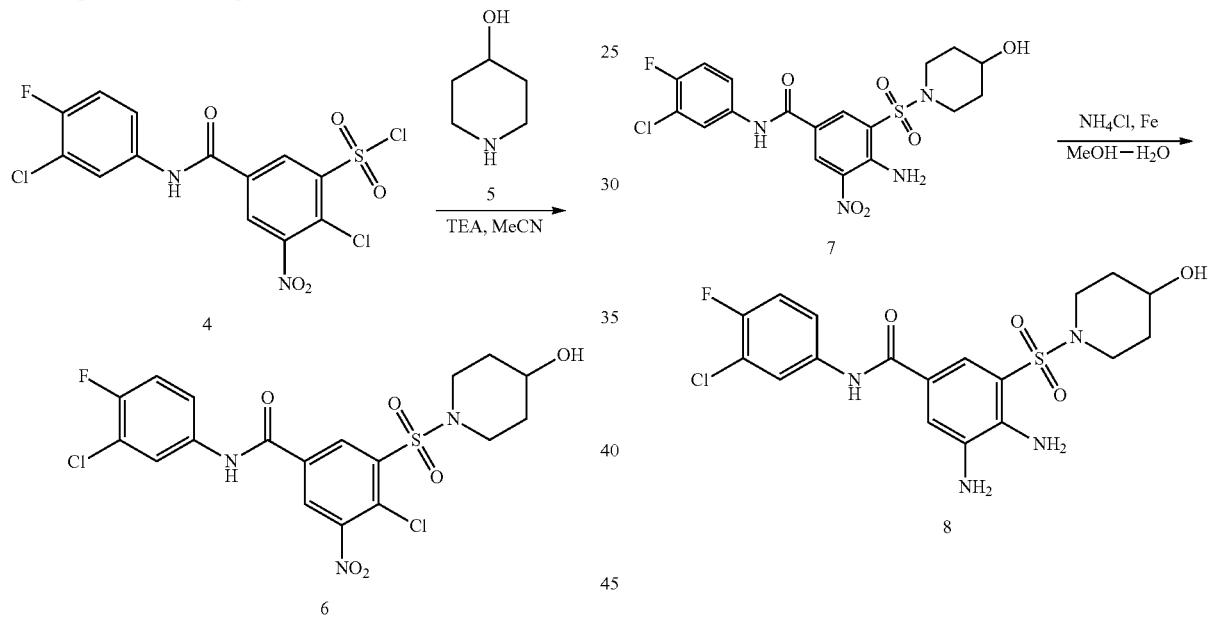

To a mixture of Compound 4 (0.8 g, crude) and piperidin-4-ol (202 mg, 2 mmol) in CH₃CN (10 mL), was added Et₃N (202 mg, 2 mmol), and stirred at room temperature for 4 hours. The mixture was diluted with EA (50 mL), the organic layer was washed with NH₄Cl (50 mL*2) and concentrated to give desired Compound 6 (0.5 g, crude) as yellow solid, which was used for the next step without further purification.

3.5 Preparation of Compound 7

A mixture of Compound 7 (0.5 g, crude), Fe (400 mg, 7 mmol) and NH₄Cl (400 mg, 7 mmol) in MeOH—H₂O (10 mL/2 mL) was heated to 70° C. for 4 hours. The mixture was filtered and washed with EA (50 mL). The filtrate was washed with saturated NH₄Cl (50 mL*2) and concentrated to give desired Compound 8 (0.3 g, crude) as white solid, which was used for the next step without purification.

3.7 Preparation of Compound 1472

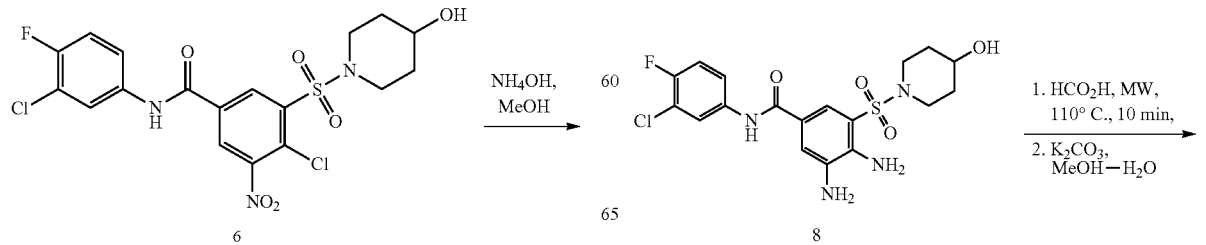

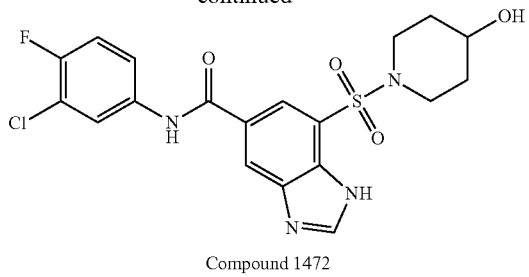

Compound 1472

A mixture of Compound 8 (0.3 g, crude) in formic acid (10 mL) was microwaved to 110° C. for 10 min. The mixture was concentrated in vacuo. The residue was dissolved in MeOH—H₂O (10 mL/2 mL), and K₂CO₃ (270 mg, 2 mmol) was added. The mixture was heated to 80° C. for 2 hours. After LCMS showed the reaction was finished, the mixture was concentrated in vacuo and extracted with EA. The organic phase was concentrated in vacuo and the residue was purified via acid preparative HPLC to give Compound 1472 (35 mg, yield 3.6% over the seven steps) as white solid.

HBV Assembly Assay

Selected compounds of the invention were assayed in the HBV assembly assay, as described elsewhere herein. The assembly assay was conducted in 96-well plate format. The assembly reactions were carried out in 50 mM Hepes buffer, pH 7.5 and 150 mM NaCl. The compounds were pre-incubated with the HBV CA protein for 15 min, and the assembly reactions were initiated by addition of NaCl. The reaction was allowed to continue for 1 hour at room temperature. The 96-well plate assembly assay consistently had Z' factors greater than 0.7 and were robust and reproducible both from plate-to-plate and day-to-day.

To determine the effect on capsid assembly, each test compound was initially screened at 4 different concentrations: 10 µM, 3 µM, 1 µM and 0.3 µM in duplicates. Primary hits were compounds that show activity in the assembly assay with $EC_{50}$ less than 10 µM and a representative group of these active compounds is illustrated in Table 2.

TABLE 2

"Activity" represents activity in HBV assembly assay ('+' indicates $EC_{50}$ < 10 µM)

| Compound | Activity | Compound | Activity |
|---|---|---|---|
| 949 | + | 1287 | + |
| 1291 | + | 1292 | + |
| 1294 | + | 1296 | + |
| 1299 | + | 1300 | + |
| 1303 | + | 1304 | + |
| 1470 | + | 1508 | + |
| 1533 | + | 1534 | + |
| 1535 | + | 1536 | + |

Dot-Blot Assay

Selected compounds, which were shown to be active in the HBV assembly assay, were tested for their activity and toxicity in cellular assay. In the first anti-viral assay, the ability of compounds to inhibit HBV replication in an HBV-producing hepatoma cell line using the dot-blot method was evaluated. Confluent monolayers of HepG2-2.2.15 cells were incubated with complete medium containing various concentrations of a test compound. Three days later, the culture medium was replaced with fresh medium containing the appropriately diluted test compound. Six days following the initial administration of the test compound, the cell culture supernatant was collected, and cell lysis was performed. The samples were applied onto Nylos membranes and DNA was immobilized to the membrane by UV cross-linking. After pre-hybridization, the HBV probe was added and the hybridization was performed overnight. The membranes were exposed to the Kodak films; antiviral activity was calculated from the reduction in HBV DNA levels ($EC_{50}$). The $EC_{50}$ for antiviral activity was calculated from the dose response curves of active compounds. Assay performance over time was monitored by the use of the standard positive control compounds ETV, BAY 41-4109, and HAP-1. Results are illustrated in Table 3.

Cytotoxity ($CC_{50}$) was measured in this same HepG2-2.2.15 cell line using a CellTiter Blue-based cytotoxicity assay employed as recommended by manufacturer (Promega). All compounds in Table 3 demonstrated low toxicity at 5 µM.

TABLE 3

"Activity" represents activity in dot-blot-assay ('+' indicates $EC_{50}$ < 10 µM)

| Compound | Activity | Compound | Activity |
|---|---|---|---|
| 949 | + | 1288 | + |
| 1290 | + | 1294 | + |
| 1298 | + | 1300 | + |
| 1302 | + | 1472 | + |
| 1508 | + | 1533 | + |
| 1535 | + | 1537 | + |

Prevention of HBV Pre-Genomic RNA (pgRNA) Incorporation

The compounds of the invention were assessed for their ability to suppress both extracellular and intracellular HBV DNA production in two different cell culture models of HBV replication. A particle-gel assay that allows quantitation of intracellular viral capsids, as well as encapsidated pre-genomic RNA and DNA, was performed. The assay relied on agarose gel separation of viral capsid from free capsid/core subunits and viral pg-RNA and DNA.

This assay revealed that the compounds of the invention prevent packaging of pre-genomic RNA into the viral capsid without significant effect on intracellular core particle levels. This effect is consistent with the biochemical activity of the compounds of the invention, which act as allosteric effectors that misdirect in vitro assembly leading to formation of aberrant, non-functional particles. The potent antiviral effect is due to that pg-RNA encapsidation is required for viral DNA synthesis.

The disclosures of each and every patent, patent application, and publication cited herein are hereby incorporated herein by reference in their entirety.

While the invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

The invention claimed is:

1. A method of treating an HBV infection in an individual in need thereof, comprising administering to the individual a therapeutically effective amount of a compound of Formula I:

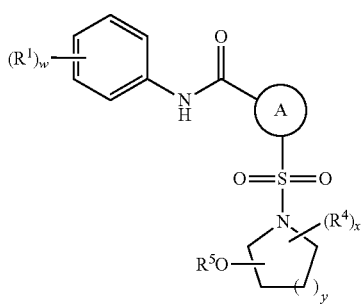

or a pharmaceutically acceptable salt thereof, wherein:

Ring A is selected from:

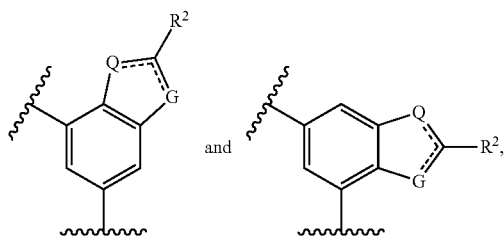

wherein:
G is N, and Q is $CH_2$ or $NR^3$, or
G is $NR^3$, and Q is CH or N, or
G is CH, and Q is $NR^3$, or
G is $CH_2$, and Q is N; and
---- represents a single or double bond;
$R^1$ in each occurrence is independently selected from halo, —CN, $C_{1-6}$alkyl, —$OC_{1-6}$alkyl, and —$NO_2$, wherein the $C_{1-6}$alkyl is optionally substituted with one to three halo;
$R^2$ in each occurrence is independently selected from hydrogen, halo, and $C_{1-6}$alkyl;
$R^3$ is selected from H and $C_{1-6}$alkyl;
$R^4$ in each occurrence is independently selected from halo, $C_{1-6}$alkyl, monocyclic 5 to 7-membered carbocyclyl, monocyclic 5 to 7-membered heterocyclyl, —$OR^{4a}$, —$SR^{4a}$, and —$N(R^{4a})_2$ wherein the $C_{1-6}$alkyl, monocyclic 5 to 7-membered carbocyclyl, and monocyclic 5 to 7-membered heterocyclyl are optionally substituted with one or more $R^{40}$;
$R^{4a}$ in each occurrence is independently selected from H, $C_{1-6}$alkyl, monocyclic 5 to 7-membered carbocyclyl, and monocyclic 5 to 7-membered heterocyclyl, wherein said $C_{1-6}$alkyl, monocyclic 5 to 7-membered carbocyclyl, and monocyclic 5 to 7-membered heterocyclyl, are optionally and independently substituted with one or more $R^{40}$;
$R^5$ is selected from H and $C_{1-6}$alkyl;
$R^{40}$ in each occurrence is independently selected from halo, —CN, $C_{1-6}$ alkyl, monocyclic 5 to 7-membered carbocyclyl, monocyclic 5 to 7-membered heterocyclyl, —$OR^{40a}$, —$SR^{40a}$, —$N(R^{40a})_2$, —$NO_2$, —$C(O)R^{40b}$, and —$C(O)_2R^{40a}$;

$R^{40a}$ in each occurrence is independently selected from H, $C_{1-6}$alkyl, monocyclic 5 to 7-membered carbocyclyl, and monocyclic 5 to 7-membered heterocyclyl;
$R^{40b}$ in each occurrence is independently selected from $C_{1-6}$alkyl, monocyclic 5 to 7-membered carbocyclyl, and monocyclic 5 to 7-membered heterocyclyl;
w is 0, 1, 2, or 3;
x is 0 or 1; and
y is 0, 1, or 2.

2. The method of claim 1, further comprising administering to the individual at least one additional therapeutic agent selected from the group consisting of a HBV polymerase inhibitor, interferon, pegylated interferon, viral entry inhibitor, viral maturation inhibitor, capsid assembly modulator, reverse transcriptase inhibitor, a TLR-agonist, AT-61 ((E)-N-(1-chloro-3-oxo-1-phenyl-3-(piperidin-1-yl)prop-1-en-2-yl)benzamide), and AT-130 ((E)-N-(1-bromo-1-(2-methoxyphenyl)-3-oxo-3-(piperidin-1-yl)prop-1-en-2-yl)-4-nitrobenzamide), and a combination thereof.

3. The method of claim 2, wherein the pegylated interferon is pegylated interferon alpha (IFN-α), pegylated interferon lambda (IFN-λ), or pegylated interferon gamma (IFN-γ).

4. The method of claim 2, wherein the reverse transcriptase inhibitor is at least one of Zidovudine, Didanosine, Zalcitabine, ddA, Stavudine, Lamivudine, Abacavir, Emtricitabine, Entecavir, Apricitabine, Atevirapine, ribavirin, acyclovir, famciclovir, valacyclovir, ganciclovir, valganciclovir, Tenofovir, Adefovir, cidofovir, Efavirenz, Nevirapine, Delavirdine, or Etravirine.

5. The method of claim 2, wherein the compound and the at least one additional therapeutic agent are co-formulated.

6. The method of claim 2, wherein the compound and the at least one additional therapeutic agent are co-administered.

7. The method of claim 2, wherein administering the compound allows for administering the at least one additional therapeutic agent at a lower dose or frequency as compared to the administering of the at least one additional therapeutic agent alone that is required to achieve similar results in prophylactically treating an HBV infection in an individual in need thereof.

8. The method of claim 2, wherein before administering the therapeutically effective amount of the compound of Formula I, the individual is known to be refractory to a compound selected from the group consisting of a HBV polymerase inhibitor, interferon, pegylated interferon, viral entry inhibitor, viral maturation inhibitor, capsid assembly modulator, AT-61 ((E)-N-(1-chloro-3-oxo-1-phenyl-3-(piperidin-1-yl)prop-1-en-2-yl)benzamide), and AT-130 ((E)-N-(1-bromo-1-(2-methoxyphenyl)-3-oxo-3-(piperidin-1-yl)prop-1-en-2-yl)-4-nitrobenzamide), and combination thereof.

9. The method of claim 2, wherein the administering of the compound reduces viral load in the individual to a greater extent compared to the administering of a compound selected from the group consisting of a HBV polymerase inhibitor, interferon, pegylated interferon, viral entry inhibitor, viral maturation inhibitor, capsid assembly modulator, AT-61 ((E)-N-(1-chloro-3-oxo-1-phenyl-3-(piperidin-1-yl)prop-1-en-2-yl)benzamide), and AT-130 ((E)-N-(1-bromo-1-(2-methoxyphenyl)-3-oxo-3-(piperidin-1-yl)prop-1-en-2-yl)-4-nitrobenzamide), and combination thereof.

10. The method of claim 2, wherein the administering of the compound causes a lower incidence of viral mutation and/or viral resistance than the administering of a compound selected from the group consisting of a HBV polymerase inhibitor, interferon, pegylated interferon, viral entry inhibitor, viral maturation inhibitor, capsid assembly modulator, AT-61 ((E)-N-(1-chloro-3-oxo-1-phenyl-3-(piperidin-1-yl)

prop-1-en-2-yl)benzamide), and AT-130 ((E)-N-(1-bromo-1-(2-methoxyphenyl)-3-oxo-3-(piperidin-1-yl)prop-1-en-2-yl)-4-nitrobenzamide), and combination thereof.

11. The method of claim 3, wherein the pegylated interferon alpha is PEGASYS.

12. The method of claim 1, wherein the compound of Formula I is selected from the group consisting of:

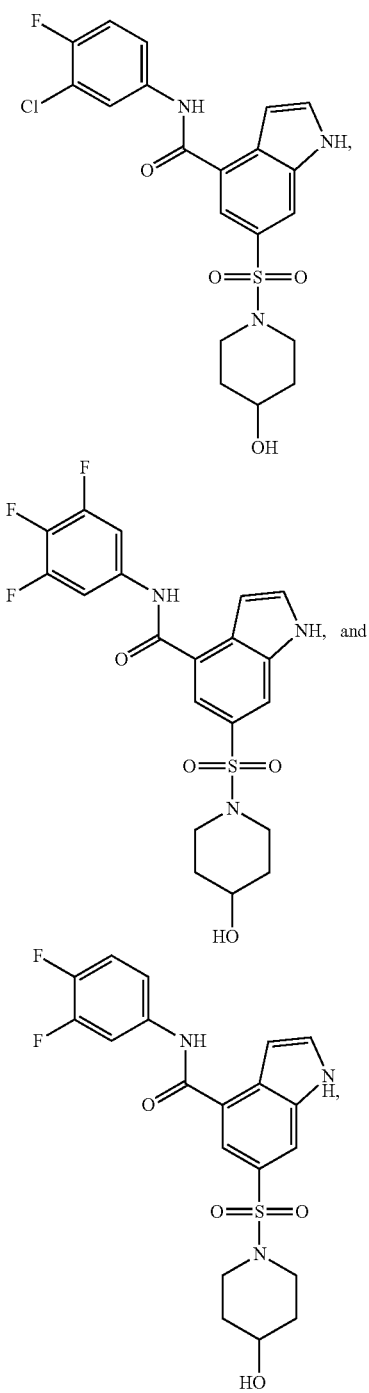

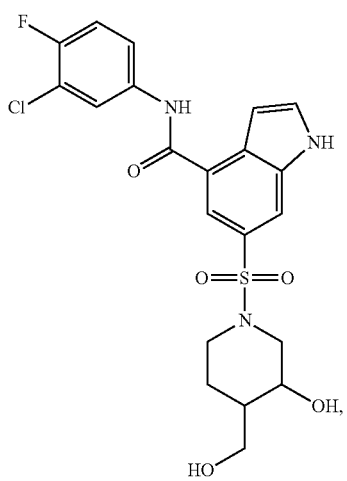

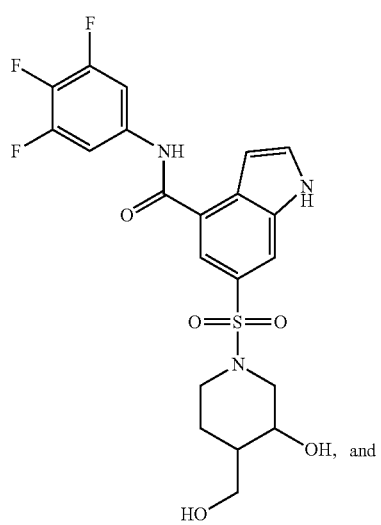

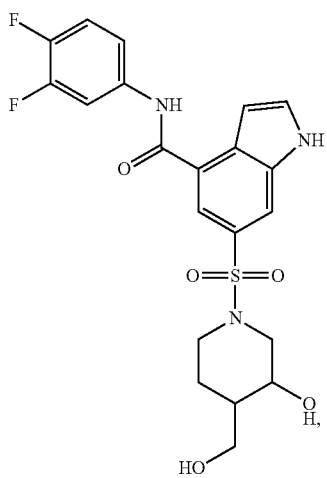

or a pharmaceutically acceptable salt thereof.

13. The method of claim 1, wherein the compound of Formula I is selected from the group consisting of:

or a pharmaceutically acceptable salt thereof.

14. The method of claim 1, wherein the compound of Formula I is selected from the group consisting of:

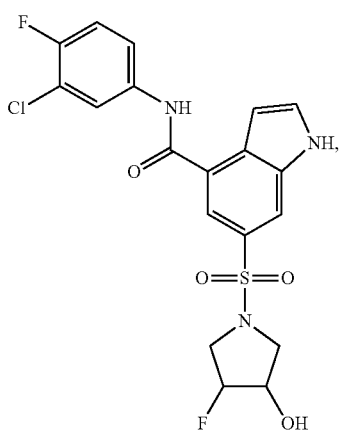
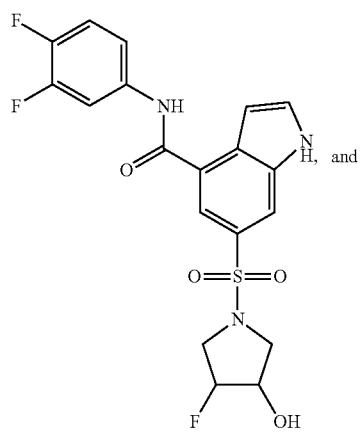
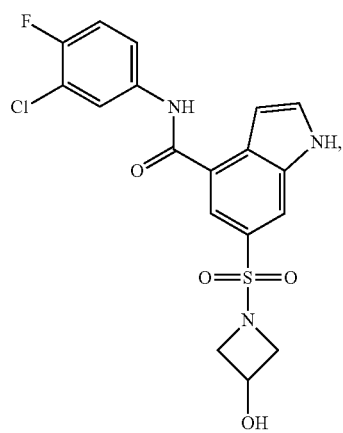
or a pharmaceutically acceptable salt thereof.
15. The method of claim 1, wherein the compound of Formula I is selected from the group consisting of:
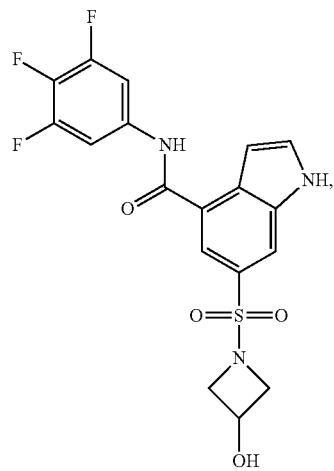
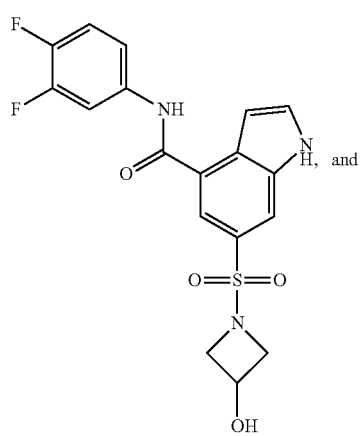
or a pharmaceutically acceptable salt thereof.

16. The method of claim 1, wherein the compound of Formula I is selected from the group consisting of:
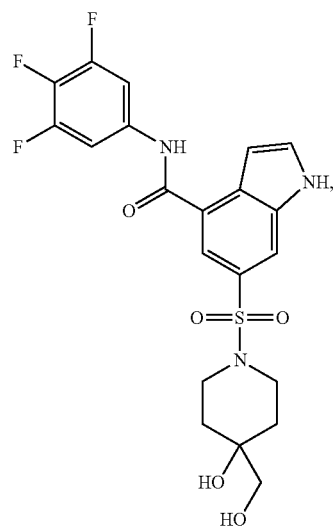
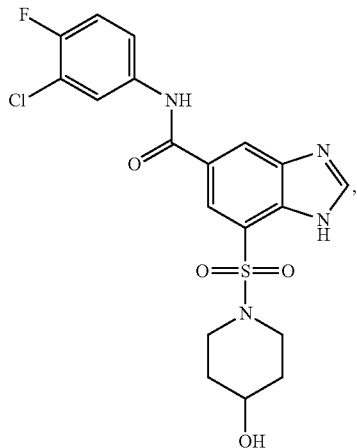
-continued
or a pharmaceutically acceptable salt thereof.
17. The method of claim 1, wherein the compound of Formula I is selected from the group consisting of:
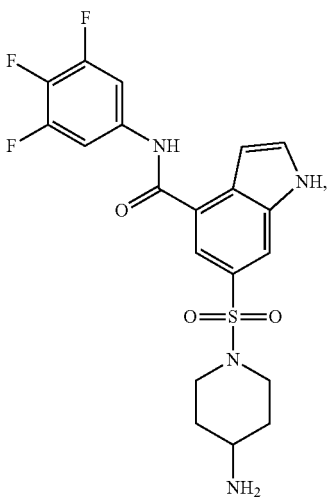
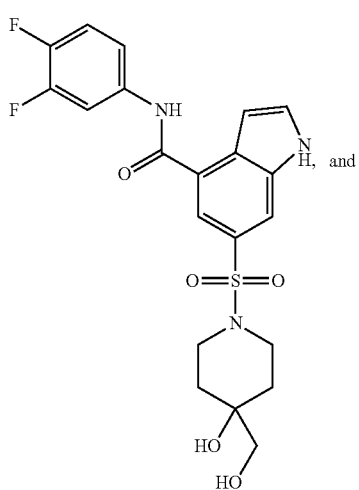
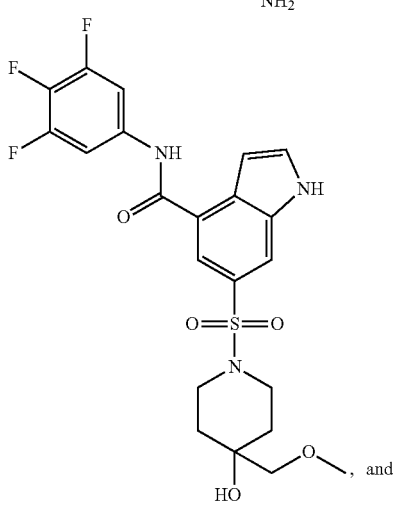

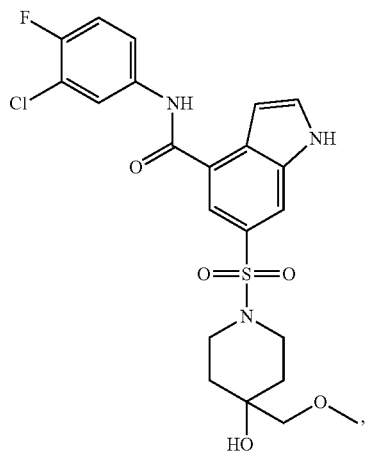
or a pharmaceutically acceptable salt thereof.
18. The method of claim 1, wherein the compound of Formula I is selected from the group consisting of:
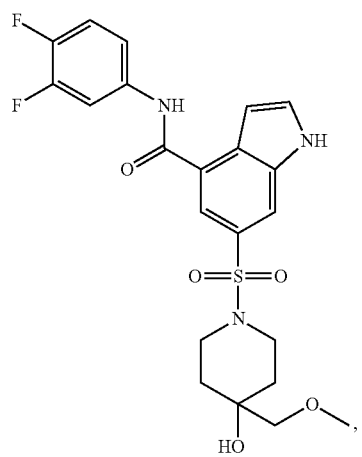
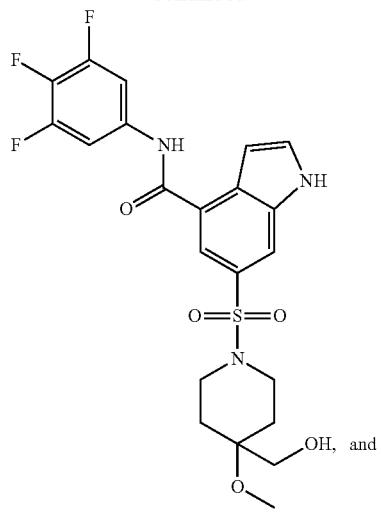
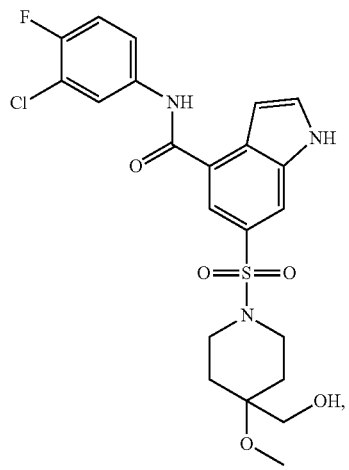
or a pharmaceutically acceptable salt thereof.
* * * * *